(12) United States Patent
Neikirk et al.

(10) Patent No.: US 12,005,145 B2
(45) Date of Patent: *Jun. 11, 2024

(54) METAL OXIDE ENCAPSULATED DRUG COMPOSITIONS AND METHODS OF PREPARING THE SAME

(71) Applicant: Applied Materials, Inc., Santa Clara, CA (US)

(72) Inventors: Colin C. Neikirk, Mountain View, CA (US); Jonathan Frankel, Los Gatos, CA (US)

(73) Assignee: Applied Materials, Inc., Santa Clara, CA (US)

( * ) Notice: Subject to any disclaimer, the term of this patent is extended or adjusted under 35 U.S.C. 154(b) by 126 days.

This patent is subject to a terminal disclaimer.

(21) Appl. No.: 17/695,687

(22) Filed: Mar. 15, 2022

(65) Prior Publication Data

US 2022/0202732 A1    Jun. 30, 2022

Related U.S. Application Data

(63) Continuation of application No. 16/249,885, filed on Jan. 16, 2019, now Pat. No. 11,311,491.

(30) Foreign Application Priority Data

Jan. 16, 2018 (IN) .............................. 201841001745

(51) Int. Cl.
| | | |
|---|---|---|
| A61K 9/50 | (2006.01) | |
| A61J 3/07 | (2006.01) | |
| A61K 31/405 | (2006.01) | |
| A61K 31/424 | (2006.01) | |
| A61K 31/43 | (2006.01) | |
| A61K 31/506 | (2006.01) | |
| A61K 31/519 | (2006.01) | |
| A61K 31/7048 | (2006.01) | |
| A61K 47/58 | (2017.01) | |
| C07K 16/22 | (2006.01) | |
| C07K 16/28 | (2006.01) | |
| C07K 16/32 | (2006.01) | |
| C23C 16/40 | (2006.01) | |
| C23C 16/44 | (2006.01) | |
| C23C 16/455 | (2006.01) | |
| C23C 16/458 | (2006.01) | |

(52) U.S. Cl.
CPC .............. *A61K 9/5089* (2013.01); *A61J 3/07* (2013.01); *A61K 9/501* (2013.01); *A61K 31/405* (2013.01); *A61K 31/424* (2013.01); *A61K 31/43* (2013.01); *A61K 31/506* (2013.01); *A61K 31/519* (2013.01); *A61K 31/7048* (2013.01); *A61K 47/58* (2017.08); *C07K 16/22* (2013.01); *C07K 16/2833* (2013.01); *C07K 16/32* (2013.01); *C23C 16/40* (2013.01); *C23C 16/403* (2013.01); *C23C 16/405* (2013.01); *C23C 16/4417* (2013.01); *C23C 16/45525* (2013.01); *C23C 16/45555* (2013.01); *C23C 16/458* (2013.01); *C07K 2317/24* (2013.01); *C07K 2317/94* (2013.01)

(58) Field of Classification Search
CPC .... A61K 9/5089; A61K 47/58; A61K 31/506; A61K 31/519; A61K 31/405; A61K 31/43; A61K 9/501; A61K 31/7048; A61K 31/424; C07K 16/32; C07K 16/22; C07K 16/2833; C07K 2317/94; A61J 3/07; C23C 16/40; C23C 16/45525; C23C 16/405; C23C 16/4417; C23C 16/403; C23C 16/45555; C23C 16/458

See application file for complete search history.

(56) References Cited

U.S. PATENT DOCUMENTS

| | | | |
|---|---|---|---|
| 4,289,871 | A | 9/1981 | Rowan et al. |
| 6,165,512 | A | 12/2000 | Mezaache et al. |
| 6,613,383 | B1 | 9/2003 | George et al. |
| 7,357,910 | B2 | 4/2008 | Phillips et al. |
| 8,524,772 | B2 | 9/2013 | Arad et al. |
| 8,697,097 | B2 | 4/2014 | Nonomura et al. |
| 10,166,198 | B2 | 1/2019 | Carlsson et al. |

(Continued)

FOREIGN PATENT DOCUMENTS

| | | |
|---|---|---|
| DE | 10307568 | 9/2004 |
| EP | 1621187 | 2/2006 |

(Continued)

OTHER PUBLICATIONS

Balaji et al., "Nano-zirconia-Evaluation of its antioxidant and anticancer activity," Journal of Photochemistry & Photobiology, B: Biology, May 1, 2017, 170: 125-133.

(Continued)

*Primary Examiner* — Shirley V Gembeh
(74) *Attorney, Agent, or Firm* — Fish & Richardson P.C.

(57) ABSTRACT

A method of preparing a pharmaceutical composition having a drug-containing core enclosed by one or more metal oxide materials is provided. The method includes the sequential steps of (a) loading the particles comprising the drug into a reactor, (b) applying a vaporous or gaseous metal precursor to the particles in the reactor, (c) performing one or more pump-purge cycles of the reactor using inert gas, (d) applying a vaporous or gaseous oxidant to the particles in the reactor, and (e) performing one or more pump-purge cycles of the reactor using inert gas. The temperature of the particles does not exceed 35° C. This produces a pharmaceutical composition comprising a drug containing core enclosed by one or more metal oxide materials.

18 Claims, 33 Drawing Sheets

(56) References Cited

U.S. PATENT DOCUMENTS

| | | |
|---|---|---|
| 10,478,402 B2 | 11/2019 | Carlsson et al. |
| 10,512,796 B2 | 12/2019 | Toledano et al. |
| 10,603,284 B2 | 3/2020 | Hoppu et al. |
| 11,311,491 B2 | 4/2022 | Neikirk et al. |
| 2003/0026989 A1 | 2/2003 | George et al. |
| 2003/0118642 A1 | 6/2003 | Norman et al. |
| 2004/0037883 A1 | 2/2004 | Zhou et al. |
| 2005/0266078 A1 | 12/2005 | Jorda et al. |
| 2006/0263479 A1 | 11/2006 | Boghani et al. |
| 2007/0036850 A1 | 2/2007 | Roehrich et al. |
| 2007/0280895 A1 | 12/2007 | Weimer et al. |
| 2009/0186968 A1 | 7/2009 | Zong et al. |
| 2010/0136110 A1 | 6/2010 | Tasaki et al. |
| 2010/0297251 A1 | 11/2010 | Timmons et al. |
| 2010/0303722 A1 | 12/2010 | Jin et al. |
| 2011/0091563 A1 | 4/2011 | Kurasawa et al. |
| 2011/0300224 A1 | 12/2011 | Murpani et al. |
| 2012/0201860 A1 | 8/2012 | Weimer et al. |
| 2013/0202790 A1 | 8/2013 | Li et al. |
| 2013/0336866 A1 | 12/2013 | Soeger et al. |
| 2013/0337056 A1 | 12/2013 | Lehtonen et al. |
| 2015/0250731 A1 | 9/2015 | Hoppu et al. |
| 2016/0081945 A1 | 3/2016 | Carlsson et al. |
| 2017/0007545 A1 | 1/2017 | Hoppu et al. |
| 2017/0333359 A1 | 11/2017 | Goldstein et al. |
| 2019/0216742 A1 | 7/2019 | Neikirk et al. |
| 2020/0197313 A1 | 6/2020 | Hoppu et al. |
| 2020/0338008 A1 | 10/2020 | Wang et al. |
| 2021/0217609 A1 | 7/2021 | Kagaya |
| 2021/0378971 A1 | 12/2021 | Wang et al. |
| 2022/0105048 A1 | 4/2022 | Wang et al. |
| 2022/0296530 A1 | 9/2022 | Neikirk |
| 2023/0059964 A1 | 2/2023 | Hoppu et al. |
| 2023/0097519 A1 | 3/2023 | Wang et al. |
| 2023/0355536 A1 | 11/2023 | Wang et al. |
| 2023/0364023 A1 | 11/2023 | Wang et al. |

FOREIGN PATENT DOCUMENTS

| | | |
|---|---|---|
| IN | 802MUM2000 | 2/2005 |
| JP | 2004-269384 | 9/2004 |
| JP | 2005-060309 | 3/2005 |
| JP | 2005-520796 | 7/2005 |
| JP | 2008-013480 | 1/2008 |
| JP | 2008-539801 | 11/2008 |
| JP | 2010-501538 | 1/2010 |
| JP | 2011-063627 | 3/2011 |
| JP | 2012-051810 | 3/2012 |
| JP | 2014-510066 | 4/2014 |
| JP | 2015-528487 | 9/2015 |
| JP | 2016-519155 | 6/2016 |
| KR | 10-20140011358 | 1/2014 |
| KR | 10-20160013050 | 2/2016 |
| KR | 10-2016-0090478 | 8/2016 |
| KR | 10-20170094046 | 8/2017 |
| WO | WO 1990/002546 | 3/1990 |
| WO | WO 1996/22030 | 7/1996 |
| WO | WO 2005/044224 | 5/2005 |
| WO | WO 2006/090640 | 8/2006 |
| WO | WO 2007/015243 | 2/2007 |
| WO | WO 2008/023184 | 2/2008 |
| WO | WO 2010/135107 | 11/2010 |
| WO | WO 2011/011207 | 1/2011 |
| WO | WO 2011/141486 | 11/2011 |
| WO | WO 2012/116814 | 9/2012 |
| WO | WO 2019/143744 | 7/2019 |
| WO | WO 2020/219583 | 10/2020 |

OTHER PUBLICATIONS

Kääriäinen et al., "Surface modification of acetaminophen particles by atomic layer deposition," International Journal of Pharmaceutics, Jun. 15, 2017, 525(1):160-74.

Choi et al., "Rapid vapor deposition SiO2 thin film deposited at a low temperature using tris (tert-pentoxy) silanol and trimethylaluminum," Materials Chemistry and Physics, Nov. 15, 2013, 142(2-3):614-8.

Li et al., "Oxide bioceramics: inert ceramic materials in medicine and dentistry," Handbook of Biomaterial Properties, 1998, 4 pages.

Mftah et al., "Physicochemical properties, cytotoxicity, and antimicrobial activity of sulphated zirconia nanoparticles," International Journal of Nanomedicine, 2015:10 765-774.

Won et al., "Effect of Catalyst Layer Density and Growth Temperature in Rapid Atomic Layer Deposition of Silica Using Tris (tert-pentoxy) silanol," ACS Applied Materials & Interfaces, May 25, 2011, 3(5):1633-9.

Zirconia Biomaterials, Arya(ed)., 2022, 4 pages.

"Pharmaceutical Preparations," European Pharmacopoeia 8.0, Apr. 2013, 756-758.

Andrew et al., "Sustained Release of a Monoclonal Antibody from Electrochemically Prepared Mesoporous Silicon Oxide," Advanced Functional Materials, Dec. 2010, 20(23):4168-4174.

Arin et al., "Characterization of ZnO—TiO2 and zinc titanate nanoparticles synthesized by hydrothermal process," Res Chem Intermed, 2017, 43:3183-3195.

Arl et al., "SiO2 thin film growth through a pure atomic layer deposition technique at room temperature," Royal Society of Chemistry, May 2020, 10:18073-18081.

Extended European Search Report in European Appln. No. 19741437.8, dated Oct. 12, 2021, 10 pages.

Groner et al., "Low-temperature Al2O3 atomic layer deposition," Chemistry of Materials, Chemistry of Materials, American Chemical Society, US, Feb. 24, 2004, 16(4):639-645.

International Search Report and Written Opinion in International Application No. PCT/US2019/013881, dated May 8, 2019, 11 pages.

Kaariainen et al., "Surface modification of acetaminophen particles by atomic layer deposition," International Journal of Pharmaceutics, Apr. 18, 2017, 525(1):160-174.

Klaus et al., "SiO2 Chemical Vapor Deposition at Room Temperature Using SiCl4 and H 2 O with an NH 3 Catalyst," Journal of the Electrochemical Society, 2000, 147(7):2658-2664.

Knez et al., "Synthesis and Surface Engineering of Complex Nanostructures by Atomic Layer Deposition," Advanced Materials, Nov. 5, 2007, 19(21):3425-3438.

Knez et al., "Atomic Layer Deposition on Biological Macromolecules: Metal Oxide Coating of Tobacco Mosaic Virus and Ferritin," Nano Letters, 2006, 6(6):1172-1177.

Li et al., "Nanoparticle Multilayers: Surface Modification of Photosensitive Drug Microparticles for Increased Stability and In Vitro Bioavailability," Journal of Nanoscience and Nanotechnology, Sep. 2006, 6(9-10):3252-3260.

Martino et al., "A new pure paracetamol for direct compression: The orthorhombic form," International Journal of Pharmaceutics, 1996, 128:1-8.

Office Action in Chinese Appln. No. 201980012924.4, dated May 6, 2022, 6 pages (with English translation).

Office Action in Chinese Appln. No. 201980012924.4, dated Nov. 23, 2021, 12 pages (with English translation).

Office Action in Indian Appln. No. 202047034175, dated Nov. 26, 2020, 6 pages.

Office Action in Japanese Appln. No. 2020-560122, dated Sep. 14, 2021, 12 pages (with English translation).

Office Action in Korean Appln. No. 10-2020-7023286, dated Jan. 25, 2022, 10 pages (with English translation).

Patel et al., "Ensuring Better Control of Granulation," Pharmaceutical Manufacturing, Aug. 7, 2008, http://www.pharmamanufacturing/com/articles/2008/096/, 11 pages.

Prescott et al., "On Powder Flowability," Pharmaceutical Technology, Oct. 2000, 14 pages.

Shah et al., "Comparative Evaluation of Flow for Pharmaceutical Powders and Granules," AAPS PharmSciTech, 2008, 9(1):250-258.

Siddiqi et al., "Properties of Zinc Oxide Nanoparticles and Their Activity Against Microbes," Nanoscale Research Letters, 2018, 13:141, 13 pages.

(56) References Cited

OTHER PUBLICATIONS

Singh et al., "Microencapsulation: A promising technique for controlled drug delivery," Res. Pharnn. Sci., 2010, 5(2):65-77.
Verheezen et al., "Milling of agglomerates in an impact mill," Int. J. Pharm., 2004, 278:165-172.
Wikipedia.com [online], "Titanium Oxide," retrieved on Aug. 20, 2021, retrieved from URL <https://en.wikipedia.org/wiki/Titanium_oxide>, 1 page.
Wu et al., "Preparation and properties of composite particles made by nano zinc oxide coated with titanium dioxide," J. Mater. Sci., 2006, 41:5845-5850.
www.ahdictionary.com [online], "Granule," retrieved on Aug. 9, 2019, retrieved from URL <https:www.ahdictionary.com/word/search/html?q=granule>, 3 pages.
Xie et al., "Atomic layer deposition of TiO2 from tetrakis-dimethyl-amido titanium or Ti isopropoxide precursors and H2O," Journal of Applied Physics, 2007, 102:7 pages.
Azad et al., "Impact of Critical Material Attributes (CMAs)—Particle Shape on Miniature Pharmaceutical Unit Operations," AAPS PharmSciTech, Apr. 2021, 22(3):1-11.
Lee et al., "Low temperature atomic layer deposition of SiO2 thin films using diisopropylaminosilane and ozone," Ceramics International, Feb. 1, 2017, 43(2):2095-2099.
Nam et al., "Low-temperature, high-growth-rate ALD of SiO2 using aminodisilane precursor," Applied Surface Science, Aug. 15, 2019, 485:381-390.
Hakim et al., "Conformal nanocoating of zirconia nanoparticles by atomic layer deposition in a fluidized bed reactor," Nanotechnology, 2005, 16:S375-S381.
Huo et al., "Pre-Treatment with Zirconia Nanoparticles Reduces Inflammation Induced by the Pathogenic H5N1 Influenza Virus," International Journal of Nanomedicine, 2020, 15:661-674.

Figure 19 : Fragmentation pattern of main Palbociclib peak (448.2) as detected by MALDI-MS/MS.

| Mass | Predicted Modifications |
|---|---|
| Avastin Control | |
| 149364.7184 | 1*G0 (NGA2)/G1(2760.5716) + 5*Oxidation (M)(15.9994) + 2*pyroGlu (E)(-18.0153) |
| 149203.7758 | 2*G0 (NGA2)(1299.2142) + 5*Oxidation (M)(15.9994) + 2*pyroGlu (E)(-18.0153) |
| 149525.9668 | 1*G0 (NGA2)/G2(2922.7148) + 2*Oxidation (M)(15.9994) |
| 149462.4541 | 1*G0 (NGA2)/G1(2760.5716) + 11*Oxidation (M)(15.9994) + 2*pyroGlu (E)(-18.0153) |
| 149622.4356 | 1*G0F (NGA2F)/G1F(3052.8593) |
| Avastin Coated | |
| 149364.6928 | 1*G0 (NGA2)/G1(2760.5716) + 5*Oxidation (M)(15.9994) + 2*pyroGlu (E)(-18.0153) |
| 149526.0062 | 1*G0 (NGA2)/G2(2922.7148) + 2*Oxidation (M)(15.9994) |
| 149463.0575 | 1*G0 (NGA2)/G1(2760.5716) + 11*Oxidation (M)(15.9994) + 2*pyroGlu (E)(-18.0153) |
| 149624.1364 | 1*G0 (NGA2)/G2(2922.7148) + 11*Oxidation (M)(15.9994) + 2*pyroGlu (E)(-18.0153) |
| 149203.8475 | 2*G0 (NGA2)(1299.2142) + 5*Oxidation (M)(15.9994) + 2*pyroGlu (E)(-18.0153) |
| 149783.1643 | 1*G0F (NGA2F)/G2F(3215.8025) |

Table 1: Major heterogeneities detected via LC-MS for intact Avastin samples. Analysis was done using Agilent MassHunter Qualitative Analysis and BioConfirm software. Samples were run in duplicates. Unmatched modification is highlighted in yellow.

| Avastin | Sequence Coverage (%) |
|---|---|
| Coated | 98.95 |
| Control | 98.65 |

Table 2: Sequence coverage of double digested Avastin samples when compared against *in-silico* digested Avastin sequence using Agilent MassHunter Qualitative Analysis and BioConfirm software. Matching threshold was kept at 10ppm.

FIG. 24

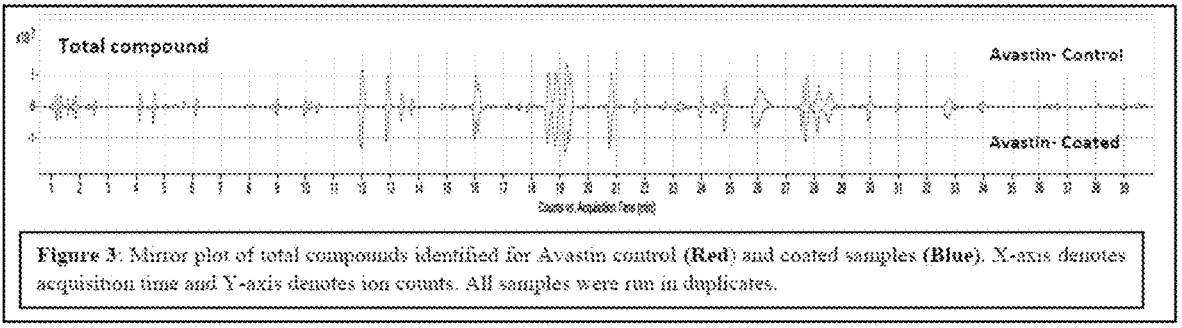

Figure 3: Mirror plot of total compounds identified for Avastin control (Red) and coated samples (Blue). X-axis denotes acquisition time and Y-axis denotes ion counts. All samples were run in duplicates.

FIG. 25

| Sample | Alpha helix | Beta sheet | Random coil | Beta turn |
|---|---|---|---|---|
| Avastin control | 9.532 | 56.616 | 10.464 | 23.388 |
| Avastin coated | 9.517 | 56.601 | 10.456 | 23.425 |

Table 4. Quantifying secondary structure for Avastin samples as calculated from the percentage transmittance values obtained from FTIR spectra.

FIG. 30

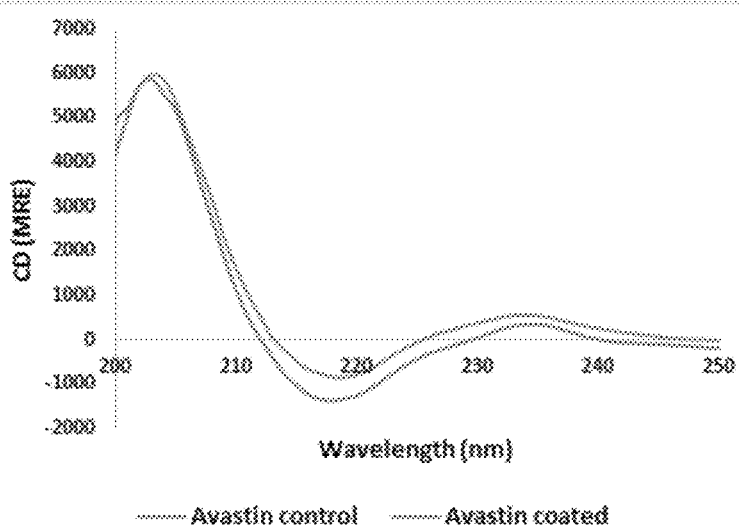

Figure 6: Far UV CD spectra of Herceptin control and coated samples. X-axis denotes wavelength and Y axis denotes molar residual ellipticity. Data represented is average of three scans.

FIG. 31

| Sample | alpha helix | Beta sheet | Random coil | beta turn |
|---|---|---|---|---|
| Herceptin control | 9.545 | 56.636 | 10.451 | 23.368 |
| Herceptin coated | 9.526 | 56.617 | 10.456 | 23.401 |

Table 12: Quantifying secondary structure for Herceptin samples as calculated from the percentage transmittance values obtained from FTIR spectra.

FIG. 36

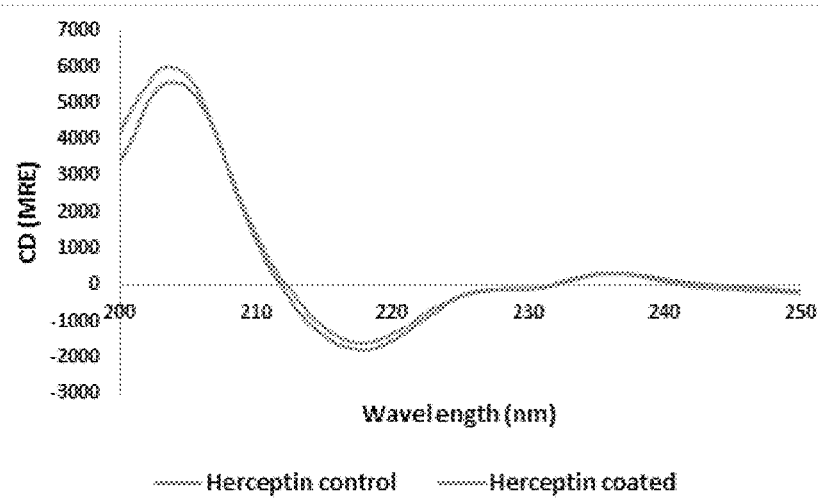

Figure 18: Far UV CD spectra of Herceptin control and coated samples. X-axis denotes wavelength and Y axis denotes molar residual ellipticity. Data represented is an average of three scans.

FIG. 37

| Sample Name | KD (M) |
|---|---|
| Herceptin-Control | 4.35E-09 |
| Herceptin-Coated | 4.87E-09 |

Table 14: The binding kinetics of different samples of mAb to Recombinant Human FcRn were estimated by SPR using Biacore X100™

FIG. 46

| Day | Sample | alpha helix | Beta sheet | Random coil | beta turn |
|---|---|---|---|---|---|
| 0 | Avastin control | 9.532 | 56.616 | 10.464 | 23.388 |
|   | Avastin coated | 9.517 | 56.601 | 10.456 | 23.425 |
| 1 | Avastin control | 9.542 | 56.576 | 10.430 | 23.452 |
|   | Avastin coated | 9.539 | 56.548 | 10.427 | 23.487 |
| 2 | Avastin control | 9.670 | 56.595 | 10.391 | 23.344 |
|   | Avastin coated | 9.654 | 56.577 | 10.382 | 23.388 |
| 3 | Avastin control | 9.548 | 56.606 | 10.462 | 23.384 |
|   | Avastin coated | 9.554 | 56.606 | 10.466 | 23.374 |
| 4 | Avastin control | 9.525 | 56.557 | 10.444 | 23.474 |
|   | Avastin coated | 9.508 | 56.562 | 10.439 | 23.491 |
| 6 | Avastin control | 9.497 | 56.693 | 10.566 | 23.244 |
|   | Avastin coated | 9.491 | 56.700 | 10.567 | 23.241 |
| 8 | Avastin control | 9.480 | 56.555 | 10.454 | 23.511 |
|   | Avastin coated | 9.482 | 56.562 | 10.463 | 23.493 |
| 10 | Avastin control | 9.503 | 56.593 | 10.448 | 23.456 |
|   | Avastin coated | 9.498 | 56.582 | 10.447 | 23.472 |

Table 7: Change in secondary structure components in Avastin. Percentage of secondary structure components in sample w.r.t time. Values are mean of technical triplicates.

FIG. 47

| Day | Sample | λmax | STDEV |
|---|---|---|---|
| 0 | Avastin control | 337 | 0.019 |
| | Avastin coated | 337 | 0.628 |
| 1 | Avastin control | 339 | 1.154 |
| | Avastin coated | 341 | 1.686 |
| 2 | Avastin control | 340 | 0.0 |
| | Avastin coated | 337 | 0.681 |
| 3 | Avastin control | 336 | 0.898 |
| | Avastin coated | 338 | 0.577 |
| 4 | Avastin control | 340 | 0.680 |
| | Avastin coated | 338 | 0.316 |
| 6 | Avastin control | 340 | 0.313 |
| | Avastin coated | 341 | 0.230 |
| 8 | Avastin control | 339 | 0.915 |
| | Avastin coated | 339 | 0.812 |
| 10 | Avastin control | 338 | 0.856 |
| | Avastin coated | 339 | 0.323 |

Table 8: Avastin λmax at different time intervals. Values indicate mean value calculated from technical

FIG. 48

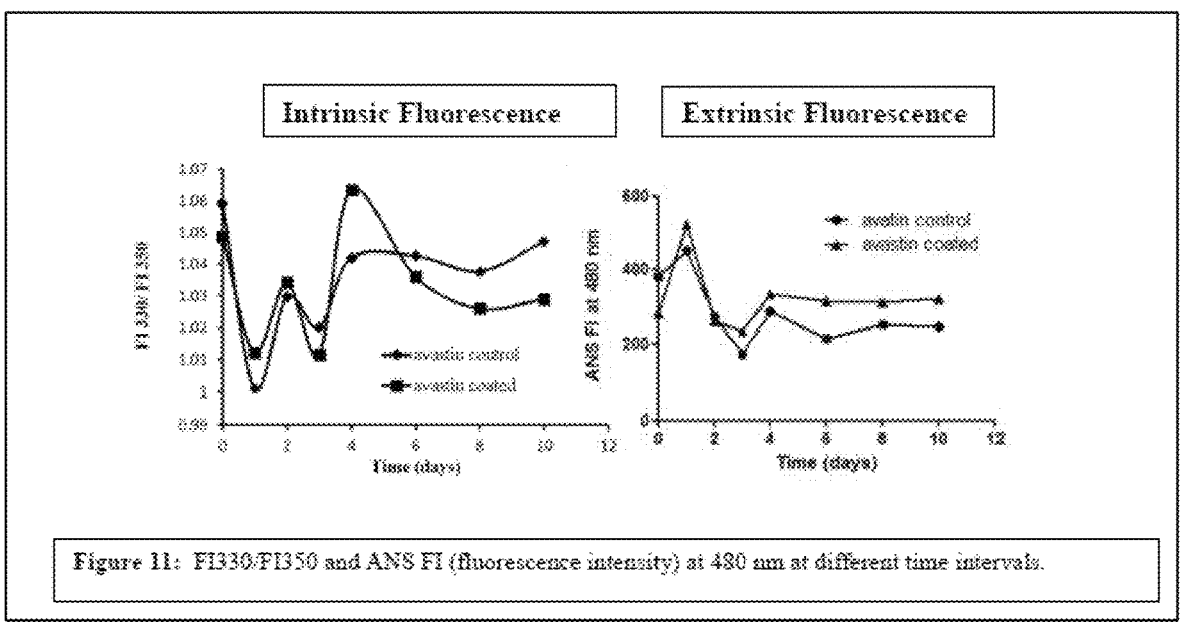

Figure 11: FI330/FI350 and ANS FI (fluorescence intensity) at 480 nm at different time intervals.

FIG. 49

| Avastin (% aggregate) 80 degrees | | |
|---|---|---|
| Time point | Control | Coated |
| Day 0 | 1.62 | 1.72 |
| Day 1 | 3.43 | 5.24 |
| Day 2 | 3.13 | 5.24 |
| Day 3 | 4.6 | 4.6 |
| Day 4 | 5.21 | 9.71 |
| Day 6 | 5.58 | 10.65 |
| Day 8 | 4.17 | 14.11 |

Table 9: Percentage of aggregates at different time intervals for Avastin samples incubated at 80°C.

| Day | Sample | Alpha helix | Beta sheet | Random coil | Beta turn |
|---|---|---|---|---|---|
| 0 | Herceptin control | 9.545 | 56.636 | 10.451 | 23.368 |
|  | Herceptin coated | 9.526 | 56.617 | 10.456 | 23.401 |
| 1 | Herceptin control | 9.549 | 56.593 | 10.439 | 23.419 |
|  | Herceptin coated | 9.531 | 56.531 | 10.418 | 23.520 |
| 2 | Herceptin control | 9.546 | 56.593 | 10.443 | 23.419 |
|  | Herceptin coated | 9.662 | 56.593 | 10.384 | 23.361 |
| 3 | Herceptin control | 9.545 | 56.631 | 10.452 | 23.371 |
|  | Herceptin coated | 9.547 | 56.617 | 10.451 | 23.385 |
| 4 | Herceptin control | 9.539 | 56.588 | 10.449 | 23.423 |
|  | Herceptin coated | 9.522 | 56.559 | 10.436 | 23.483 |
| 6 | Herceptin control | 9.547 | 56.562 | 10.441 | 23.451 |
|  | Herceptin coated | 9.514 | 56.554 | 10.445 | 23.487 |
| 8 | Herceptin control | 9.539 | 56.594 | 10.454 | 23.413 |
|  | Herceptin coated | 9.499 | 56.569 | 10.451 | 23.482 |
| 10 | Herceptin control | 9.513 | 56.598 | 10.442 | 23.447 |
|  | Herceptin coated | 9.503 | 56.583 | 10.436 | 23.478 |

Table 15: Herceptin $\lambda_{max}$ at different time intervals. Values indicate mean value calculated from technical

FIG. 52

| Day | Sample | $\lambda_{max}$ | STDEV |
|---|---|---|---|
| 0 | Herceptin control | 339 | 0.885 |
| | Herceptin coated | 338 | 0.656 |
| 1 | Herceptin control | 336 | 0.894 |
| | Herceptin coated | 340 | 0.877 |
| 2 | Herceptin control | 337 | 1.182 |
| | Herceptin coated | 340 | 0.589 |
| 3 | Herceptin control | 338 | 0.360 |
| | Herceptin coated | 339 | 0.666 |
| 4 | Herceptin control | 338 | 0.856 |
| | Herceptin coated | 340 | 0.866 |
| 6 | Herceptin control | 341 | 0.333 |
| | Herceptin coated | 339 | 0.643 |
| 8 | Herceptin control | 339 | 0.346 |
| | Herceptin coated | 339 | 0.346 |
| 10 | Herceptin control | 340 | 0.013 |
| | Herceptin coated | 339 | 0.319 |

Table 16: Herceptin $\lambda_{max}$ at different time intervals. Values indicate mean value calculated from technical triplicates.

FIG. 53

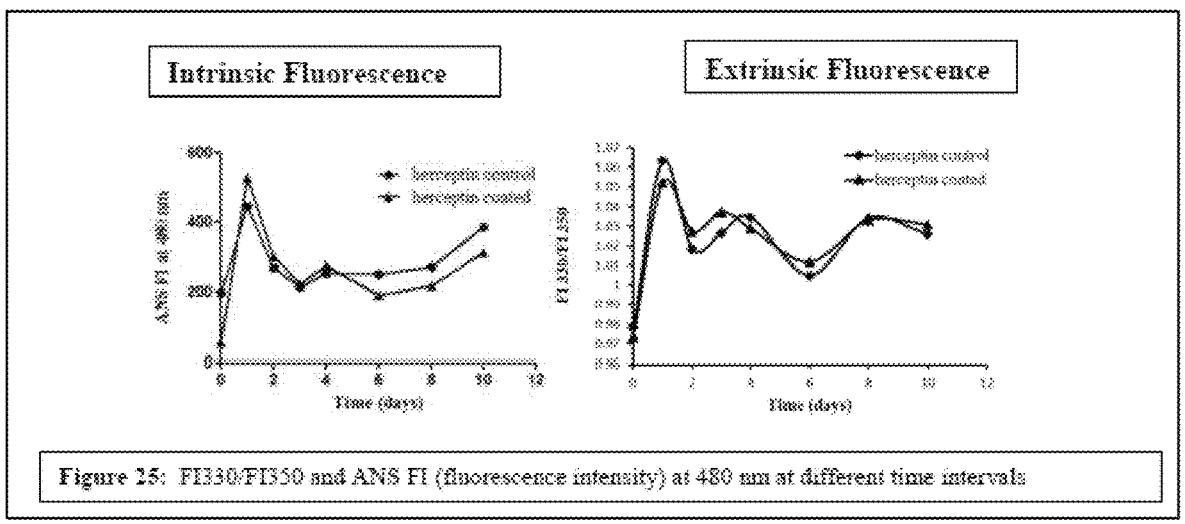

Figure 25: FI330/FI350 and ANS FI (fluorescence intensity) at 480 nm at different time intervals

FIG. 54

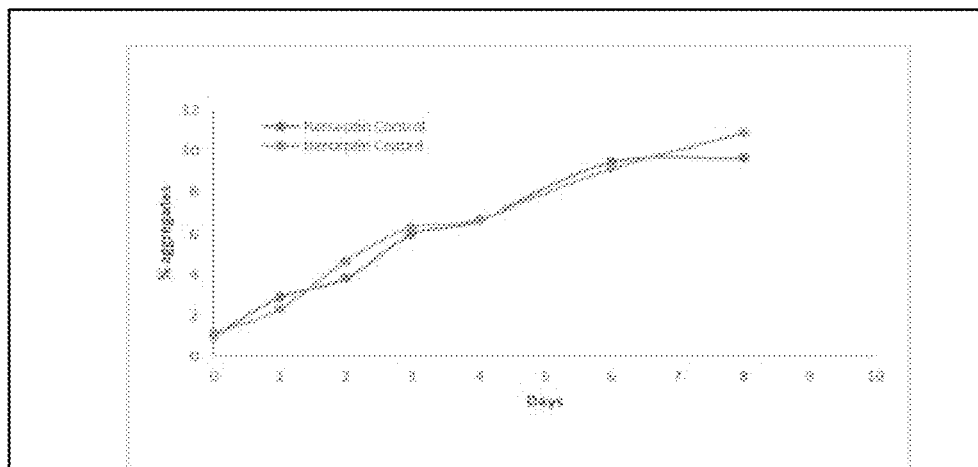

Figure 26: Increase in percentage of aggregates at different time intervals in Herceptin samples incubated at 80°C.

FIG. 55

| Table: Herceptin (% aggregate) at 80°C | | |
|---|---|---|
| Time point | Lab control | Coated |
| Day 0 | 1.03 | 1.15 |
| Day 1 | 2.93 | 2.36 |
| Day 2 | 3.85 | 4.7 |
| Day 3 | 6.02 | 6.36 |
| Day 4 | 6.7 | 6.76 |
| Day 6 | 9.45 | 9.13 |
| Day 8 | 9.65 | 10.89 |

Table 17: Percentage of aggregates at different time intervals

Result: Total aggregate percentage increased with respect to time but no significant difference amongst samples.

FIG. 56

METAL OXIDE ENCAPSULATED DRUG COMPOSITIONS AND METHODS OF PREPARING THE SAME

CROSS-REFERENCE TO RELATED APPLICATIONS

This application is a continuation application of and claims the benefit of priority to U.S. application Ser. No. 16/249,885, filed on Jan. 16, 2019, which claims priority to Indian Application Serial No. 201841001745, filed on Jan. 16, 2018, the contents of which are hereby incorporated by reference.

TECHNICAL FIELD

This disclosure pertains to pharmaceutical compositions and methods of preparing metal oxide encapsulated drugs at process temperatures at or below 35° C.

BACKGROUND

It is of great interest to the pharmaceutical industry to develop pharmaceutical compositions comprising drugs—e.g., small molecules, virus particles, polypeptides, polynucleotides, a mixture of polypeptides and lipids, or a mixture polynucleotides and lipids—that have enhanced flowability, longer shelf-lives, increased solubility, and contain high fraction of drug that is functional before or following administration of the pharmaceutical composition to a subject in need. These properties are likely to decrease associated manufacturing costs per therapeutic dose. These properties may also confer increased commercial value for the pharmaceutical composition or increased likelihood of government approval by (i) enabling or enhancing the safety, predictability, and success rate of the preparation method; (ii) increasing the stability of the drug over time—e.g., during preparation of pharmaceutical composition and/or in storage conditions prior to administering; (iii) increasing the solubility of the drug; and/or (iv) reducing the amount of pharmaceutical composition that must be administered to a subject in need to confer one or more therapeutic benefits. Numerous coating technologies for encapsulating drugs have been developed—e.g., polymer mesh coating, pan coating, aerosolized coating, fluidized bed reactor coating, molecular layer deposition coating, and atomic layer deposition coating. Despite advances in compositions and methods for preparing encapsulated drugs, pharmaceutical compositions prepared by known methods exhibit reduced flowability and/or contain drug that degrades—e.g., during the preparation process, and thus, there is a unmet need for new compositions and methods for preparing encapsulated drugs. The present invention addresses this need specifically for metal oxide encapsulated drugs.

SUMMARY

In one aspect, a method of preparing a pharmaceutical composition having a drug-containing core enclosed by one or more metal oxide materials is provided. The method includes the sequential steps of (a) loading the particles comprising the drug into a reactor, (b) applying a vaporous or gaseous metal precursor to the particles in the reactor, (c) performing one or more pump-purge cycles of the reactor using inert gas, (d) applying a vaporous or gaseous oxidant to the particles in the reactor, and (e) performing one or more pump-purge cycles of the reactor using inert gas. The temperature of the particles does not exceed 35° C. This produces a pharmaceutical composition comprising a drug containing core enclosed by one or more metal oxide materials.

Implementations may include one or more of the following features.

The temperature of the interior of the reactor need not exceed 35° C.

The sequential steps (b)-(e) may be repeated one or more times to increase the total thickness of the one or more metal oxide materials that enclose the core.

The reactor pressure may be allowed to stabilize following step (a), step (b), and/or step (d).

The reactor contents may be agitated prior to and/or during step (b), step (c), and/or step (e).

A subset of vapor or gaseous content may be pumped out prior to step (c) and/or step (e).

The metal oxide layer may have a thickness in range of 0.1 nm to 100 nm.

The particles may include a drug and one or more pharmaceutically acceptable excipients.

The particles may have a median particle size, on a volume average basis, between 0.1 µm and 1000 µm.

The pharmaceutical composition may be removed from the reactor and admixed with a pharmaceutically acceptable diluent or carrier.

The particles may consist essentially of the drug.

The drug may be a small molecule, virus particle, polypeptide, polynucleotide, a composition comprising polypeptide and lipid, or a composition comprising polynucleotide and lipid.

The one or more metal oxide materials may include aluminum oxide, titanium oxide, iron oxide, gallium oxide, magnesium oxide, zinc oxide, niobium oxide, hafnium oxide, tantalum oxide, lanthanum oxide, and/or zirconium dioxide.

The one or more metal oxide materials may consist of aluminum oxide and/or titanium oxide.

The oxidant may be selected from the group of water, ozone, and organic peroxide.

The polypeptide may be an antibody or antibody fragment.

The antibody or antibody fragment may be selected from the group of: alemtuzumab, bevacizumab, cetuximab, gemtuzumab ozogamicin, ipilimumab, ofatumumab, panitumumab, pembrolizumab, ranibizumab, rituximab, or trastuzumab.

The small molecule drug may be selected from the group of: acetaminophen, clarithromycin, azithromycin, ibuprofen, fluticasone propionate, salmeterol, pazopanib HCl, palbociclib, or amoxicillin potassium clavulanate.

In another aspect, a pharmaceutical composition having a drug-containing core enclosed by one or more metal oxide materials may be prepared by any of the above methods Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

BRIEF DESCRIPTION OF THE DRAWINGS

FIG. 20 is a table listing major heterogeneities detected by LC-MS in compositions of Avastin® uncoated or Avastin® coated with titanium oxide.

FIG. 23 is a table listing major heterogeneities detected by LC-MS in compositions of Herceptin® uncoated or Herceptin® coated with aluminum oxide.

FIG. 24 is a table listing percentage of sequence coverage for double digested compositions of Avastin® uncoated or Avastin® coated with titanium oxide compared to in-silico digested Avastin® sequence.

FIG. 25 is a plot showing total compounds identified in compositions of Avastin® uncoated or Avastin® coated with titanium oxide.

FIG. 30 is a table showing percentages of alpha helix, beta sheet, random coil, and beta turn for Avastin® from compositions of Avastin® uncoated or Avastin® coated with titanium oxide.

FIG. 31 is a graph showing results of far UV CD analysis of compositions of Avastin® uncoated or Avastin® coated with titanium oxide.

FIG. 36 is a table showing percentages of alpha helix, beta sheet, random coil, and beta turn for Herceptin® from compositions of Herceptin® uncoated or Herceptin® coated with aluminum oxide.

FIG. 37 is a graph showing results of far UV CD analysis of compositions of Herceptin® uncoated or Herceptin® coated with aluminum oxide.

FIG. 46 is a table showing KD values quantified from results shown in FIG. 46.

FIG. 47 is a table showing percentages of secondary structure of Avastin® over time as measured by FTIR from compositions of Avastin® uncoated or Avastin® coated with titanium oxide.

FIG. 48 is a table showing λmax of Avastin® over time as measured by FTIR from compositions of Avastin® uncoated or Avastin® coated with titanium oxide.

FIG. 49 are graphs showing results of intrinsic and extrinsic fluorescence of Avastin® over time from compositions of Avastin® uncoated or Avastin® coated with titanium oxide.

FIG. 52 is a table showing percentages of secondary structure of Herceptin® over time as measured by FTIR from compositions of Herceptin® uncoated or Herceptin® coated with aluminum oxide.

FIG. 53 is a table showing λmax of Herceptin® over time as measured by FTIR from compositions of Herceptin® uncoated or Herceptin® coated with aluminum oxide.

FIG. 54 are graphs showing results of intrinsic and extrinsic fluorescence of Herceptin® over time from compositions of Herceptin® uncoated or Herceptin® coated with aluminum oxide.

FIG. 55 is a graph showing percentage of aggregates as measured by SEC of Herceptin® over time from compositions of Herceptin® uncoated or Herceptin® coated with aluminum oxide.

FIG. 56 is a table showing percentage of aggregates quantified from results presented in FIG. 55.

DETAILED DESCRIPTION

Figures 1, 2:
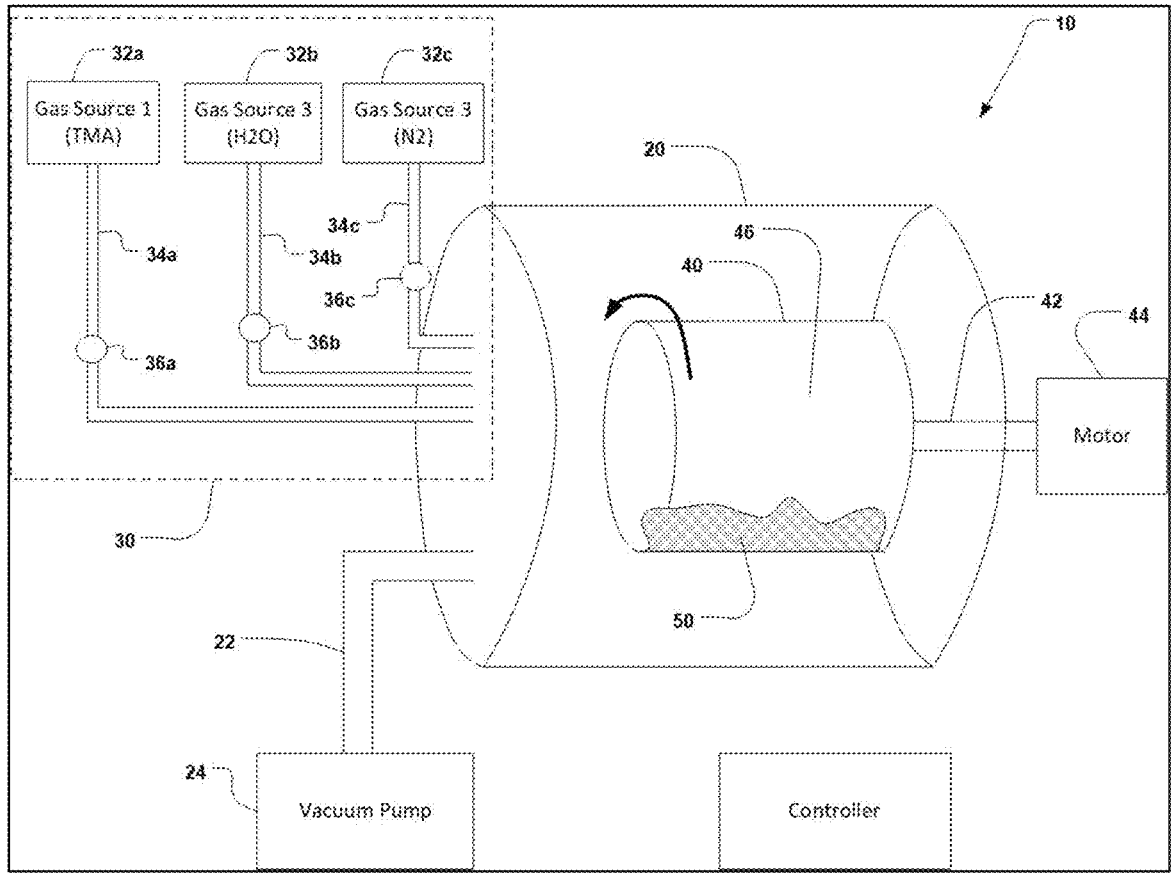
FIG. 1 is a schematic illustration of a rotary reactor for ALD and/or CVD coating of particles, e.g., drugs.
FIG. 2 is a table showing representative process conditions for the method.

The present disclosure provides methods of preparing pharmaceutical compositions comprising drugs encapsulated by one or more layers of metal oxide. Such pharmaceutical compositions have enhanced flowability, solubility, stability over time and contain a high fraction of drug that is functional before or following administration of the pharmaceutical composition to a subject in need. Overall, the provided methods of preparing the pharmaceutical compositions are able to safely, reliably, and predictably generate pharmaceutical compositions with the aforementioned properties. As result, the provided pharmaceutical compositions and methods of preparing metal oxide encapsulated drugs have increased therapeutic value, increased commercial value, and lower production cost per therapeutic dose.

The manufacture of the advantageous pharmaceutical compositions was enabled by the discovery that sequentially applying vaporous or gaseous metal precursor and vaporous or gaseous oxidant (and performing one or more pump-purge cycles using an inert gas after each application of said metal or oxidant) allowed the entire method to be preformed at lower temperatures—e.g., not exceeding 35° C. Known methods of coating drug with metal oxide using vaporous or gaseous precursors when performed at temperatures lower than 50° C. do not yield pharmaceutical compositions with improved properties due to elevated levels of oxidant (e.g., water) in the reactor as the temperature is decreased below 50° C. The elevated and persistent levels of oxidant in the reactor can negatively affect the reaction (and adsorption) of the metal precursors and oxidant with the particle surface and with each other. Additionally, the elevated levels of oxidant in the reactor can interfere with the ability to remove unreacted metal precursor, gaseous byproduct from the reaction of metal precursor with exposed hydroxyl groups on the substrate or on surface of particle, and/or unreacted oxidant that are not incorporated into metal oxide layers around the drug, which can lead to formation of contaminating metal oxide particles and/or to reduced predictability concerning the number and uniformity of metal oxide layers formed around the drug. Without wishing to be bound to a particular theory, the step of pump-purge cycles may mediate a kinetic effect to knockoff oxidant molecules on the particle surface and on the internal surface of the reactor that are kinetically, not thermodynamically, trapped there. As a result, problematic moisture content in the reactor is reduced below the amount expected based on thermodynamic principles, well known in the art, that are dictated by the pressure, temperature, and number of molecules in the reactor.

Herein are method is provided that utilizes a mechanical system and a chemical engineering process. The present disclosure also provides exemplary components and operating conditions of said system and process and exemplary drug substrates, vaporous and gaseous metal precursors, and vaporous and gaseous oxidants.

Drug

The term "drug," in its broadest sense includes small molecule, virus particle—polypeptide, polynucleotide, polypeptide, a composition comprising polypeptide and lipid, and a composition comprising polynucleotide and lipid. The drug could be selected from the group consisting of an analgesic, an anesthetic, an anti-inflammatory agent, an anthelmintic, an anti-arrhythmic agent, an antiasthma agent, an antibiotic, an anticancer agent, an anticoagulant, an antidepressant, an antidiabetic agent, an antiepileptic, an antihistamine, an antitussive, an antihypertensive agent, an antimuscarinic agent, an antimycobacterial agent, an antineoplastic agent, an antioxidant agent, an antipyretic, an immunosuppressant, an immunostimulant, an antithyroid agent, an antiviral agent, an anxiolytic sedative, a hypnotic, a neuroleptic, an astringent, a bacteriostatic agent, a beta-adrenoceptor blocking agent, a blood product, a blood substitute, a bronchodilator, a buffering agent, a cardiac inotropic agent, a chemotherapeutic, a contrast media, a corticosteroid, a cough suppressant, an expectorant, a mucolytic, a diuretic, a dopaminergic, an antiparkinsonian agent, a free radical scavenging agent, a growth factor, a haemostatic, an immunological agent, a lipid regulating agent, a muscle relaxant, a protein, a peptide, a polypeptide, a parasympathomimetic, a parathyroid calcitonin, a biphosphonate, a prostaglandin, a radio-pharmaceutical, a hormone, a sex hormone, an anti-allergic agent, an appetite stimulant, an anoretic, a steroid, a sympathomimetic, a thyroid agent, a vaccine, a vasodilator and a xanthine.

Exemplary types of small molecule drugs include, but are not limited to, acetaminophen, clarithromycin, azithromycin, ibuprofen, fluticasone propionate, salmeterol, pazopanib HCl, palbociclib, and amoxicillin potassium clavulanate. Exemplary types of polypeptide drugs include, but are not limited to, proteins (e.g., antibodies), peptide fragments (e.g., antibody fragments), alemtuzumab, bevacizumab, cetuximab, gemtuzumab ozogamicin, ipilimumab, ofatumumab, panitumumab, pembrolizumab, ranibizumab, rituximab, or trastuzumab. Exemplary types of polynucleotide drugs include, but are not limited to, one or more of DNA, RNA including messenger mRNA (mRNA), hybrids thereof, RNAi-inducing agents, RNAi agents, siRNAs, shRNAs, miRNAs, antisense RNAs, ribozymes, catalytic DNA, triple helix formation inducing RNAs, aptamers, and vectors. Exemplary types of lipids include, but are not limited to fats, waxes, sterol-containing metabolites, vitamins, fatty acids, glycerolipids, glycerophospholipids, sphingolipids, saccharolipids, and polyketides, and prenol lipids.

In the present disclosure, the drug loaded into the reactor may be in powdered form. Exemplary methods of preparing drugs in powdered form include, but are not limited to processes utilizing lyophilization, freeze-drying, precipitation, and dry compacting.

Metal Oxide Material

The term "metal oxide material," in its broadest sense includes all materials formed from the reaction of elements considered metals with oxygen-based oxidants. Exemplary metal oxide materials include, but are not limited to, aluminum oxide, titanium dioxide, iron oxide, gallium oxide, magnesium oxide, zinc oxide, niobium oxide, hafnium oxide, tantalum oxide, lanthanum oxide, and zirconium dioxide. Exemplary oxidants include, but are not limited to, water, ozone, and inorganic peroxide.

Atomic Layer Deposition (ALD)

Atomic layer deposition is a thin film deposition technique in which the sequential addition of self-limiting monolayers of an element or compound allows deposition of a film with thickness and uniformity controlled to the level of an atomic or molecular monolayer. Self-limited means that only a single atomic layer is formed at a time, and a subsequent process step is required to regenerate the surface and allow further deposition.

Chemical Vapor Deposition (CVD)

Chemical vapor deposition is a thin-film deposition technique by which an element or chemical compound is deposited on a surface by chemical reaction in the gas phase or on a surface. It is distinct from atomic layer deposition in that the deposition is not self-limited, i.e., the film will continue to grow as long as chemistry is supplied. It is distinct from physical vapor deposition in that a chemical reaction results in a deposited film that is chemically different from the precursor species.

Reactor System

The term "reactor system" in its broadest sense includes all systems that could be used to perform ALD or mixed ALD/CVD or CVD. An exemplary reactor system is illustrated in FIG. 1 and further described below.

FIG. 1 illustrates a reactor system 10 for performing coating of particles, e.g., thermally sensitive particles, with thin-film coatings. The reactor system 10 can perform the coating using ALD and/or CVD coating conditions. The relative contribution of ALD and CVD processes to the thin-film coating can be controlled by appropriate selection of process conditions. In particular, the reactor system 10 permits a primarily ALD process, e.g., an almost entirely ALD process, to be performed at low processing temperature, e.g., below 50° C., e.g., at or below 35° C. For example, the reactor system 10 can form thin-film metal oxides on the particles primarily by ALD at temperatures of 22-35° C., e.g., 25-35° C., 25-30° C., or 30-35° C. In general, the particles can remain or be maintained at such temperatures. This can be achieved by having the reactant gases and/or the interior surfaces of the reactor chamber (e.g., the chamber 20 and drum 40 discussed below) remain or be maintained at such temperatures.

Performing ALD reaction at low temperature conditions permits coatings to be formed on the particles without degradation of the biological components, e.g., the vaccine or bio-pharma ingredients. For example, a biological component in amorphous form can be coated without breaking down the biological component or converting the biological component to a crystalline form.

The reactor system 10 includes a stationary vacuum chamber 20 which is coupled to a vacuum pump 24 by vacuum tubing 22. The vacuum pump 24 can be an industrial vacuum pump sufficient to establish pressures less than 1 Torr, e.g., 1 to 100 mTorr, e.g., 50 mTorr. The vacuum pump 24 permits the chamber 20 to be maintained at a desired pressure, and permits removal of reaction byproducts and unreacted process gases.

In operation, the reactor 10 performs the ALD thin-film coating process by introducing gaseous precursors of the coating into the chamber 20. The gaseous precursors are spiked alternatively into the reactor. This permits the ALD process to be a solvent-free process. The half-reactions of the ALD process are self-limiting, which can provide Angstrom level control of deposition. In addition, the ALD reaction can be performed at low temperature conditions, such as below 50° C., e.g., below 35° C.

The chamber 20 is also coupled to a chemical delivery system 30. The chemical delivery system 20 includes three or more gas sources 32a, 32b, 32c coupled by respective delivery tubes 34a, 34b, 34c and controllable valves 36a, 36b, 36c to the vacuum chamber 20. The chemical delivery system 30 can include a combination of restrictors, gas flow controllers, pressure transducers, and ultrasonic flow meters to provide controllable flow rate of the various gasses into the chamber 20. The chemical delivery system 30 can also include one or more temperature control components, e.g., a heat exchanger, resistive heater, heat lamp, etc., to heat or cool the various gasses before they flow into the chamber 20. Although FIG. 1 illustrates separate gas lines extending in parallel to the chamber for each gas source, two or more of the gas lines could be joined, e.g., by one or more three-way valves, before the combined line reaches the chamber 20. In addition, although FIG. 1 illustrates three gas sources, the use of four gas sources could enable the in-situ formation of laminate structures having alternating layers of two different metal oxides.

Two of the gas sources provide two chemically different gaseous reactants for the coating process to the chamber 20. Suitable reactants include any of or a combination of the following: monomer vapor, metal-organics, metal halides, oxidants, such as ozone or water vapor, and polymer or nanoparticle aerosol (dry or wet). For example, the first gas source 32a can provide gaseous trimethylaluminum (TMA) or titanium tetrachloride ($TiCl_4$), whereas the second gas source 32b can provide water vapor.

One of the gas sources can provide a purge gas. In particular, the third gas source can provide a gas that is chemically inert to the reactants, the coating, and the particles being processed. For example, the purge gas can be N2, or a noble gas, such as argon.

A rotatable coating drum 40 is held inside the chamber 20. The drum 40 can be connected by a drive shaft 42 that extends through a sealed port in a side wall of the chamber 20 to a motor 44. The motor 44 can rotate the drum at speeds of 1 to 100 rpm. Alternatively, the drum can be directly connected to a vacuum source through a rotary union.

The particles to be coated, shown as a particle bed 50, are placed in an interior volume 46 of the drum 40. The drum 40 and chamber 20 can include sealable ports (not illustrated) to permit the particles to be placed into and removed from the drum 40.

The body of the drum 40 is provided by one or more of a porous material, a solid metal, and a perforated metal. The pores through the cylindrical side walls of the drum 40 can have a dimension of 10 µm.

In operation, one of the gasses flows into chamber 20 from the chemical delivery system 30 as the drum 40 rotates. A combination of pores (1-100 um), holes (0.1-10 mm), or large openings in the coating drum serve to confine the particles in the coating drum while allowing rapid delivery of precursor chemistry and pumping of byproducts or unreacted species. Due to the pores in the drum 40, the gas can flow between the exterior of the drum 40, i.e., the reactor chamber 20, and the interior of the drum 40. In addition, rotation of the drum 40 agitates the particles to keep them separate, ensuring a large surface area of the particles remains exposed. This permits fast, uniform interaction of the particle surface with the process gas.

In some implementations, one or more temperature control components are integrated into the drum 40 to permit control of the temperature of the drum 40. For example, resistive heater, a thermoelectric cooler, or other component can in or on the side walls of the drum 40.

The reactor system 10 also includes a controller 60 coupled to the various controllable components, e.g., vacuum pump 24, gas distribution system 30, motor 44, a temperature control system, etc., to control operation of the reactor system 10. The controller 60 can also be coupled to various sensors, e.g., pressure sensors, flow meters, etc., to provide closed loop control of the pressure of the gasses in the chamber 20.

In general, the controller 60 can operate the reactor system 10 in accord with a "recipe." The recipe specifies an operating value for each controllable element as a function of time. For example, the recipe can specify the times during which the vacuum pump 24 is to operate, the times of and flow rate for each gas source 32a, 32b, 32c, the rotation rate of the motor 44, etc. The controller 60 can receive the recipe as computer-readable data (e.g., that is stored on a non-transitory computer readable medium).

The controller 60 and other computing devices part of systems described herein can be implemented in digital electronic circuitry, or in computer software, firmware, or hardware. For example, the controller can include a processor to execute a computer program as stored in a computer program product, e.g., in a non-transitory machine readable storage medium. Such a computer program (also known as a program, software, software application, or code) can be written in any form of programming language, including compiled or interpreted languages, and it can be deployed in any form, including as a standalone program or as a module, component, subroutine, or other unit suitable for use in a computing environment. In some implementations, the controller 60 is a general purpose programmable computer. In some implementations, the controller can be implemented using special purpose logic circuitry, e.g., an FPGA (field programmable gate array) or an ASIC (application specific integrated circuit).

Operation

Initially, particles are loaded into the drum 40 in the reactor system 10. The particles can have a solid core comprising a drug, e.g., one of the drugs discussed above. Once any access ports are sealed, the controller 60 operates the reactor system 10 according to the recipe in order to form the thin-film metal oxide layers on the particles.

In particular, the two reactant gases are alternately supplied to the chamber 20, with each step of supplying a reactant gas followed by a purge cycle in which the inert gas is supplied to the chamber 20 to force out the reactant gas and by-products used in the prior step. Moreover, one or more of the gases (e.g., the reactant gases and/or the inert gas) can be supplied in pulses in which the chamber 20 is filled with the gas to a specified pressure, a delay time is permitted to pass, and the chamber is evacuated by the vacuum pump 24 before the next pulse commences.

In particular, the controller 60 can operate the reactor system 10 as follows.

In a first reactant half-cycle, while the motor 44 rotates the drum 40 to agitate the particles 50:

i) The gas distribution system 30 is operated to flow the first reactant gas, e.g., TMA, from the source 32a into the chamber 20 until a first specified pressure is achieved. The specified pressure can be 0.1 Torr to half of the saturation pressure of the reactant gas.

ii) Flow of the first reactant is halted, and a specified delay time is permitted to pass, e.g., as measured by a timer in the controller. This permits the first reactant to flow through the particle bed in the drum 40 and react with the surface of the particles 50 inside the drum 40.

iii) The vacuum pump 50 evacuates the chamber 20, e.g., down to pressures below 1 Torr, e.g., to 1 to 100 mTorr, e.g., 50 mTorr.

These steps (i)-(iii) can be repeated a number of times set by the recipe, e.g., two to ten times, e.g., six times.

Next, in a first purge cycle, while the motor 44 rotates the drum to agitate the particles 50:

iv) The gas distribution system 30 is operated to flow the inert gas, e.g., N2, from the source 32c into the chamber 20 until a second specified pressure is achieved. The second specified pressure can be 1 to 100 Torr.

v) Flow of the inert gas is halted, and a specified delay time is permitted to pass, e.g., as measured by the timer in the controller. This permits the inert gas to flow through the pores in the drum 40 and diffuse through the particles 50 to displace the reactant gas and any vaporous by-products.

vi) The vacuum pump 50 evacuates the chamber 20, e.g., down to pressures below 1 Torr, e.g., to 1 to 500 mTorr, e.g., 50 mTorr.

These steps (iv)-(vi) can be repeated a number of times set by the recipe, e.g., six to twenty times, e.g., sixteen times.

In a second reactant half-cycle, while the motor 44 rotates the drum 40 to agitate the particles 50:

vii) The gas distribution system 30 is operated to flow the second reactant gas, e.g., H2O, from the source 32a into the chamber 20 until a third specified pressure is achieved. The third pressure can be 0.1 Torr to half of the saturation pressure of the reactant gas.

viii) Flow of the second reactant is halted, and a specified delay time is permitted to pass, e.g., as measured by the timer in the controller. This permits the second reactant to flow through the pores in the drum 40 and react with the surface of the particles 50 inside the drum 40.

ix) The vacuum pump 50 evacuates the chamber 20, e.g., down to pressures below 1 Torr, e.g., to 1 to 500 mTorr, e.g., 50 mTorr.

These steps (vii)-(ix) can be repeated a number of times set by the recipe, e.g., two to ten times, e.g., six times.

Next, a second purge cycle is performed. This second purge cycle can be identical to the first purge cycle, or can have a different number of repetitions of the steps (iv)-(vi) and/or different delay time and/or different pressure.

The cycle of the first reactant half-cycle, first purge cycle, second reactant half cycle and second purge cycle can be repeated a number of times set by the recipe, e.g., one to ten times.

As noted above, the coating process can be performed at low processing temperature, e.g., below 50° C., e.g., at or below 35° C. In particular, the particles can remain or be maintained at such temperatures during all of steps (i)-(ix) noted above. In general, the temperature of the interior of the reactor chamber does not exceed 35° C. during of steps (i)-(ix). This can be achieved by having the first reactant gas, second reactant gas and inert gas be injected into the chamber at such temperatures during the respective cycles. In addition, physical components of the chamber of the chamber can remain or be maintained at such temperatures, e.g., using a cooling system, e.g., a thermoelectric cooler, if necessary.

Process for Preparing Pharmaceutical Compositions Comprising Drugs Encapsulated by One or More Layers of Metal Oxide Provided are two exemplary methods for a pharmaceutical composition comprising a drug-containing core enclosed by one or more metal oxide materials. The first exemplary method includes the sequential steps of: (a) loading the particles comprising the drug into a reactor, (b) applying a vaporous or gaseous metal precursor to the substrate in the reactor, (c) performing one or more pump-purge cycles of the reactor using inert gas, (d) applying a vaporous or gaseous oxidant to the substrate in the reactor, and (e) performing one or more pump-purge cycles of the reactor using inert gas. While performing the method the temperature of the particles does not exceed 35° C.

In some embodiments of the first exemplary method, the sequential steps (b)-(e) are optionally repeated one or more times to increase the total thickness of the one or more metal oxide materials that enclose the solid core of the coated particles. In some embodiments, the reactor pressure is allowed to stabilize following step (a), step (b), and/or step (d). In some embodiments, the reactor contents are agitated prior to and/or during step (b), step (c), and/or step (e). In some embodiments, a subset of vapor or gaseous content is pumped out prior to step (c) and/or step (e).

The second exemplary method includes (e.g., consists of) the sequential steps of (a) loading the particles comprising the drug into a reactor, (b) reducing the reactor pressure to less than 1 Torr, (c) agitating the reactor contents until the reactor contents have a desired moisture content, (d) pressurizing the reactor to at least 10 Torr by adding a vaporous or gaseous metal precursor, (e) allowing the reactor pressure to stabilize, (f) agitating the reactor contents, (g) pumping out a subset of vapor or gaseous content and determining when to stop pumping based on analysis of content in reactor including metal precursor and byproduct of metal precursor reacting with exposed hydroxyl residues on substrate or on particle surface, (h) performing a sequence of pump-purge cycles of the reactor using insert gas, (i) pressuring the reactor to at least 10 Torr by adding a vaporous or gaseous oxidant, (j) allowing the reactor pressure to stabilize, (k) agitating the reactor contents, (l) pumping out a subset of vapor or gaseous content and determining when to stop pumping based on analysis of content in reactor including metal precursor, byproduct of metal precursor reacting with exposed hydroxyl residues on substrate or on particle surface, and unreacted oxidant, and (m) performing a sequence of pump-purge cycles of the reactor using insert gas. While performing the method the temperature of the particles does not exceed 35° C.

In some embodiments of the second exemplary method, the sequential steps (b)-(m) are optionally repeated one or more times to increase the total thickness of the one or more metal oxide materials that enclose the solid core of the coated particles.

Pharmaceutically Acceptable Excipients, Diluents, and Carriers

Pharmaceutically acceptable excipients include, but are not limited to:

(1) surfactants and polymers including: polyethylene glycol (PEG), polyvinylpyrrolidone (PVP), sodium lauryl sulfate, polyvinylalcohol, crospovidone, polyvinylpyrrolidone-polyvinylacrylate copolymer, cellulose derivatives, hydroxypropylmethyl cellulose, hydroxypropyl cellulose, carboxymethylethyl cellulose, hydroxypropyllmethyl cellulose phthalate, polyacrylates and polymethacrylates, urea, sugars, polyols, carbomer and their polymers, emulsifiers, sugar gum, starch, organic acids and their salts, vinyl pyrrolidone and vinyl acetate;

(2) binding agents such as cellulose, cross-linked polyvinylpyrrolidone, microcrystalline cellulose;

(3) filling agents such as lactose monohydrate, lactose anhydrous, microcrystalline cellulose and various starches;

(4) lubricating agents such as agents that act on the flowability of a powder to be compressed, including colloidal silicon dioxide, talc, stearic acid, magnesium stearate, calcium stearate, silica gel;

(5) sweeteners such as any natural or artificial sweetener including sucrose, xylitol, sodium saccharin, cyclamate, aspartame, and acesulfame K;

(6) flavoring agents;
(7) preservatives such as potassium sorbate, methylparaben, propylparaben, benzoic acid and its salts, other esters of parahydroxybenzoic acid such as butylparaben, alcohols such as ethyl or benzyl alcohol, phenolic chemicals such as phenol, or quaternary compounds such as benzalkonium chloride;
(8) buffers;
(9) Diluents such as pharmaceutically acceptable inert fillers, such as microcrystalline cellulose, lactose, dibasic calcium phosphate, saccharides, and/or mixtures of any of the foregoing;
(10) wetting agents such as corn starch, potato starch, maize starch, and modified starches, and mixtures thereof;
(11) disintegrants; such as croscarmellose sodium, crospovidone, sodium starch glycolate; and
(12) effervescent agents such as effervescent couples such as an organic acid (e.g., citric, tartaric, malic, fumaric, adipic, succinic, and alginic acids and anhydrides and acid salts), or a carbonate (e.g., sodium carbonate, potassium carbonate, magnesium carbonate, sodium glycine carbonate, L-lysine carbonate, and arginine carbonate) or bicarbonate (e.g. sodium bicarbonate or potassium bicarbonate)

EXAMPLES

The following materials and methods were used in the Examples set forth herein.

Example 1: Prepare Particles Comprising Drug Encapsulated by Uniform, Thin Layers of Aluminum Oxide Coating with Nanometer Level Precision with Process Temperatures at or Below 35° C.

In this Example, one of the methods disclosed for preparing metal oxide encapsulated drugs is performed and the data is presented. In this Example, the vaporous or gaseous metal precursor is tri-methyl aluminum (TMA), the byproduct gaseous methane is formed after TMA reacts with exposed hydroxyl groups on the particles or on surface of the coated particles, and the oxidant is water vapor.

Method
In brief, the method comprised the sequential steps of:
(a) loading particles comprising the drug into a reactor;
(b) reducing the reactor pressure to less than 1 Torr;
(c) agitating the reactor contents until the reactor contents has a desired water content by
performing residual gas analysis (RGA) to monitor levels of water vapor in the reactor;
(d) pressurizing the reactor to at least 1 Torr by adding a vaporous or gaseous TMA;
(e) allowing the reactor pressure to stabilize;
(f) agitating the reactor contents;
(g) pumping out a subset of vapor or gaseous content, including gaseous methane and unreacted TMA, and determining when to stop pumping by performing RGA to monitor levels of gaseous methane and unreacted TMA in the reactor.
(h) performing a sequence of pump-purge cycles on the reactor using nitrogen gas;
(i) pressuring the reactor to at least 1 Torr by adding water vapor;
(j) allowing the reactor pressure to stabilize;
(k) agitating the reactor contents;
(l) pumping out a subset of vapor or gaseous content, including water vapor, and determining when to stop pumping by performing RGA to monitor levels of water vapor in the reactor;
(m) performing a sequence of pump-purge cycles on the reactor using nitrogen gas.

While performing the method the internal reactor temperature did not exceed 35° C. Additionally, the steps of (b)-(m) were repeated more than once to increase the total thickness of the aluminum oxide that enclose said solid core. FIG. 2 includes representative process conditions for performing this method.

Figure 3:
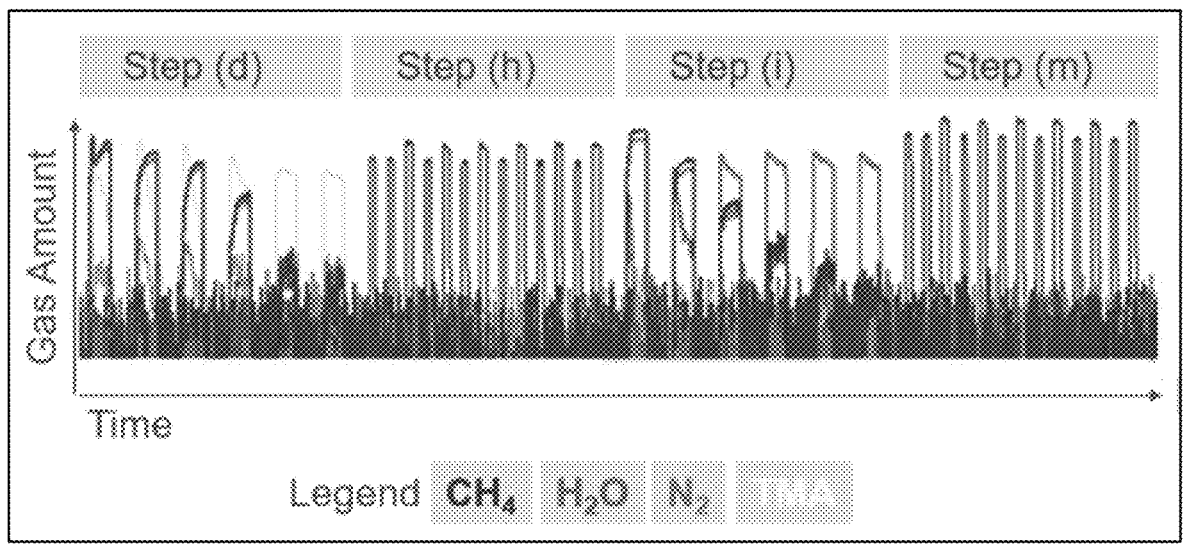
FIG. 3 is a graph depicting representative residual gas analysis traces measuring during steps (d), (h), (i), and (m) for one cycle of the method.
Figure 4:
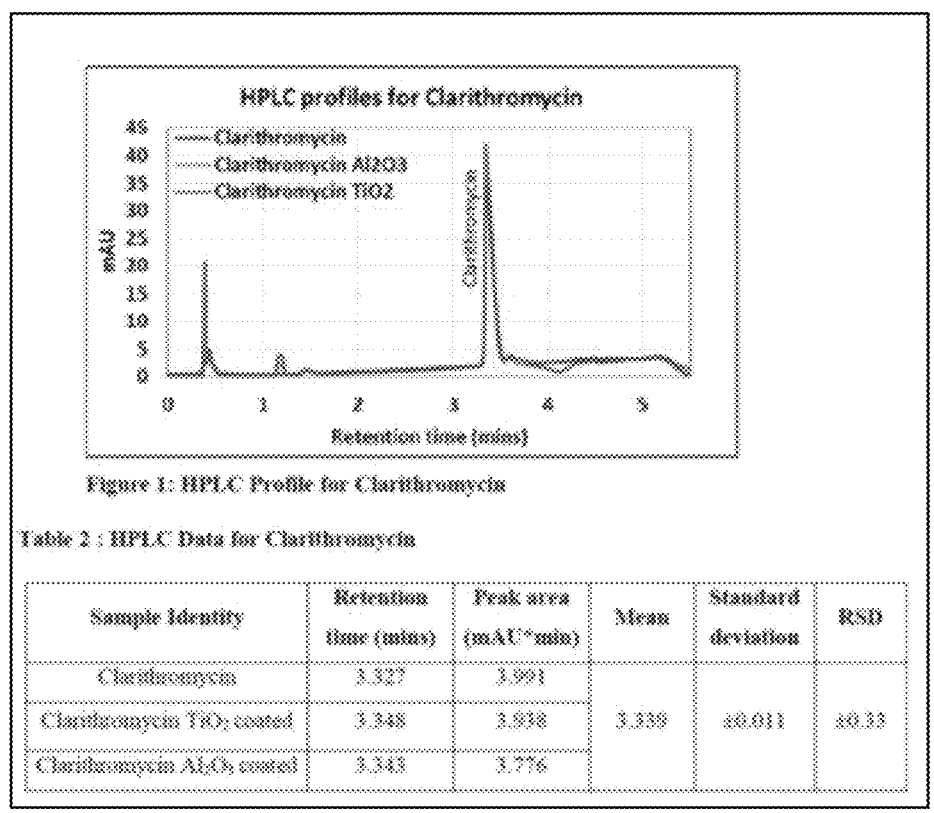
FIG. 4 (Top) is a graph showing overlaid HPLC chromatograms clarithromycin from compositions comprising clarithromycin uncoated, clarithromycin coated with aluminum oxide, or clarithromycin coated with titanium oxide; (Bottom) is a table showing values quantified from the HPLC chromatograms.
Figure 5:
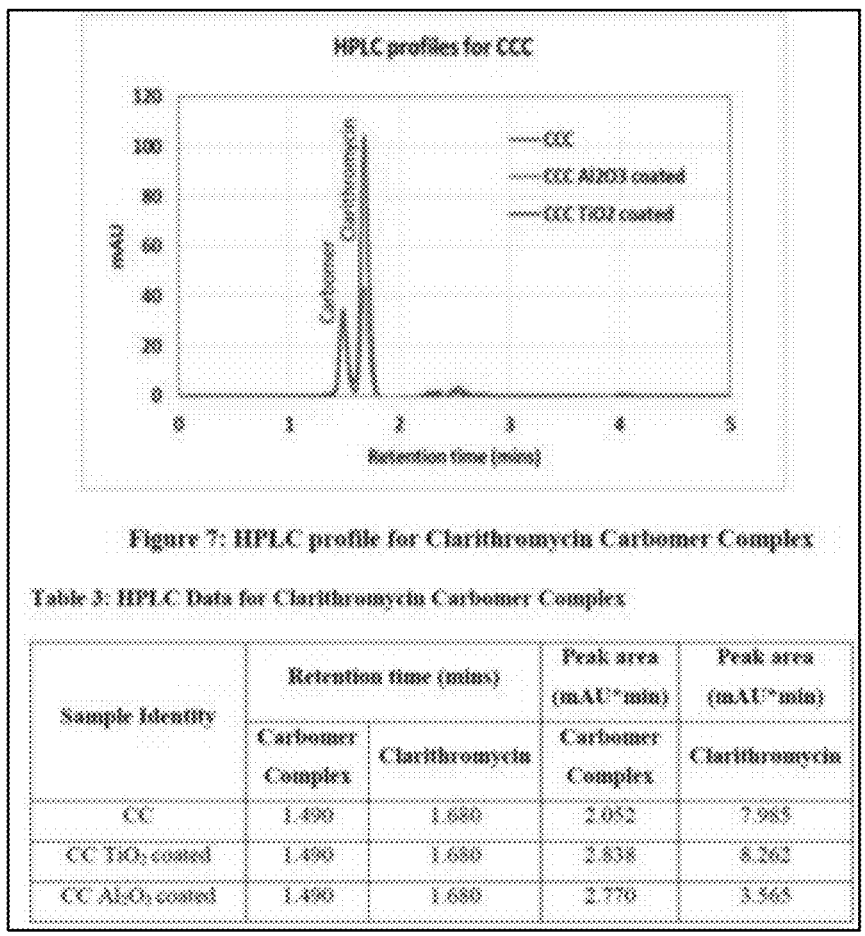
FIG. 5 (Top) is a graph showing overlaid HPLC chromatograms of clarithromycin carbomer complex (CCC) from compositions comprising CCC uncoated, CCC coated with aluminum oxide, or CCC coated with titanium oxide; (Bottom) is a table showing values quantified from the HPLC chromatograms.
Figure 6:
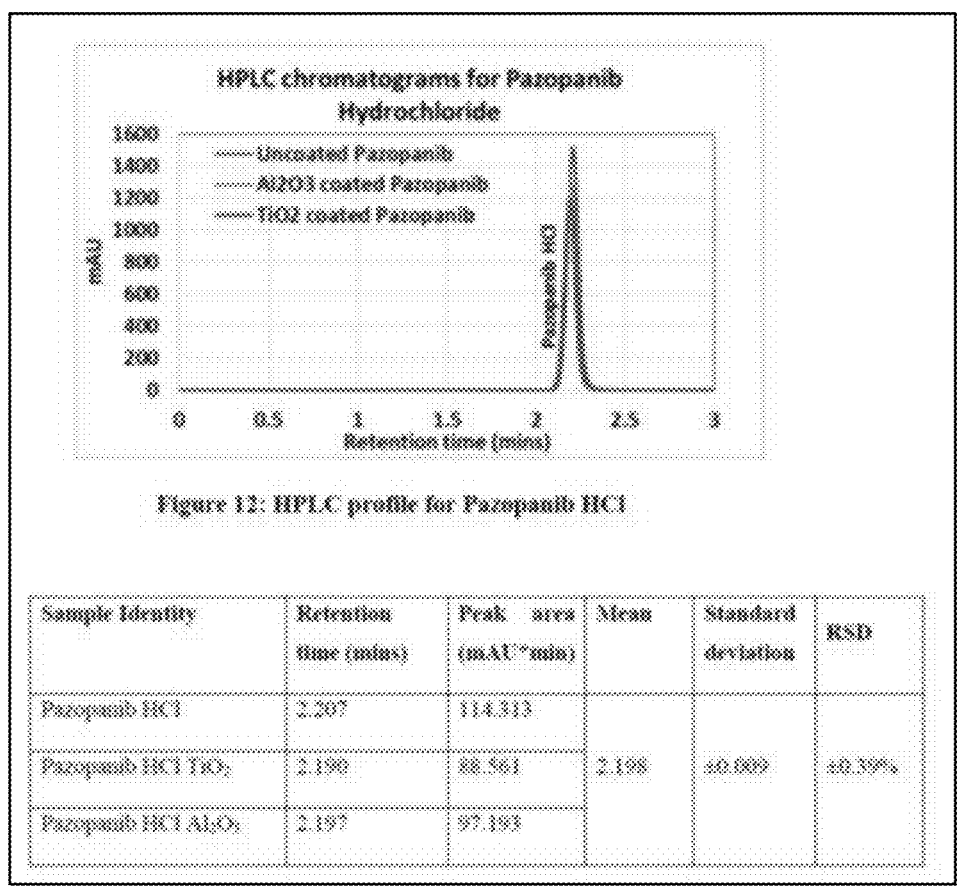
FIG. 6 (Top) is a graph showing overlaid HPLC chromatograms of pazopanib from compositions comprising pazopanib uncoated, pazopanib coated with aluminum oxide, or pazopanib coated with titanium oxide analyzed; (Bottom) is a table showing values quantified from the HPLC chromatograms.
Figure 7:
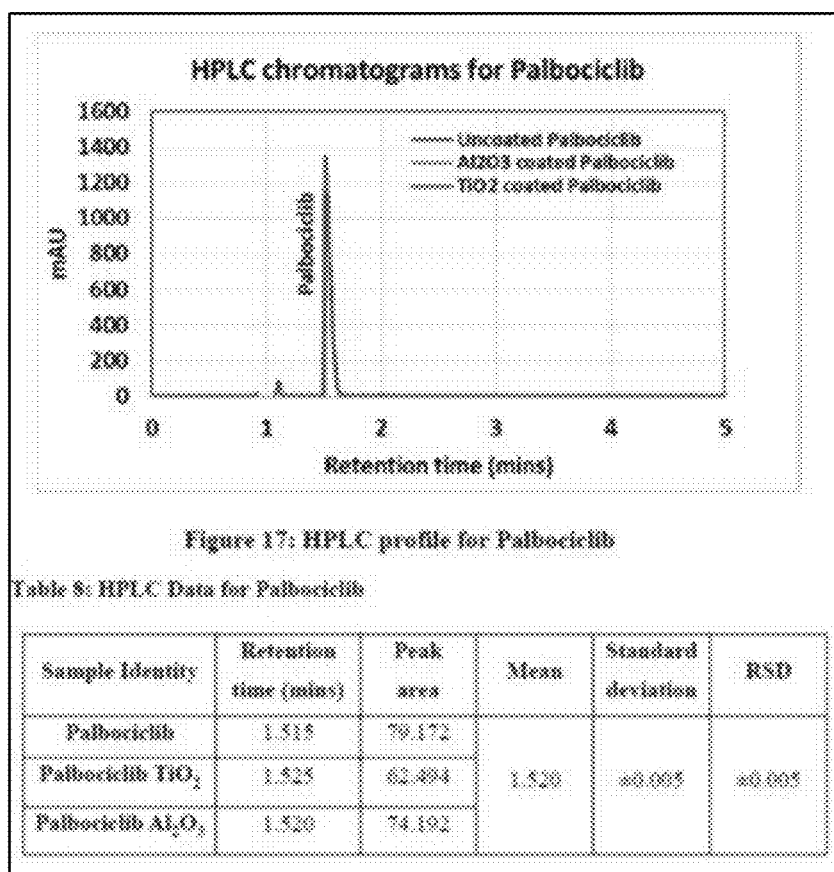
FIG. 7 (Top) is a graph showing overlaid HPLC chromatograms of palbociclib from compositions comprising clarithromycin palbociclib uncoated, palbociclib coated with aluminum oxide, or palbociclib coated with titanium oxide; (Bottom) is a table showing values quantified from the HPLC chromatograms.
Figure 8:
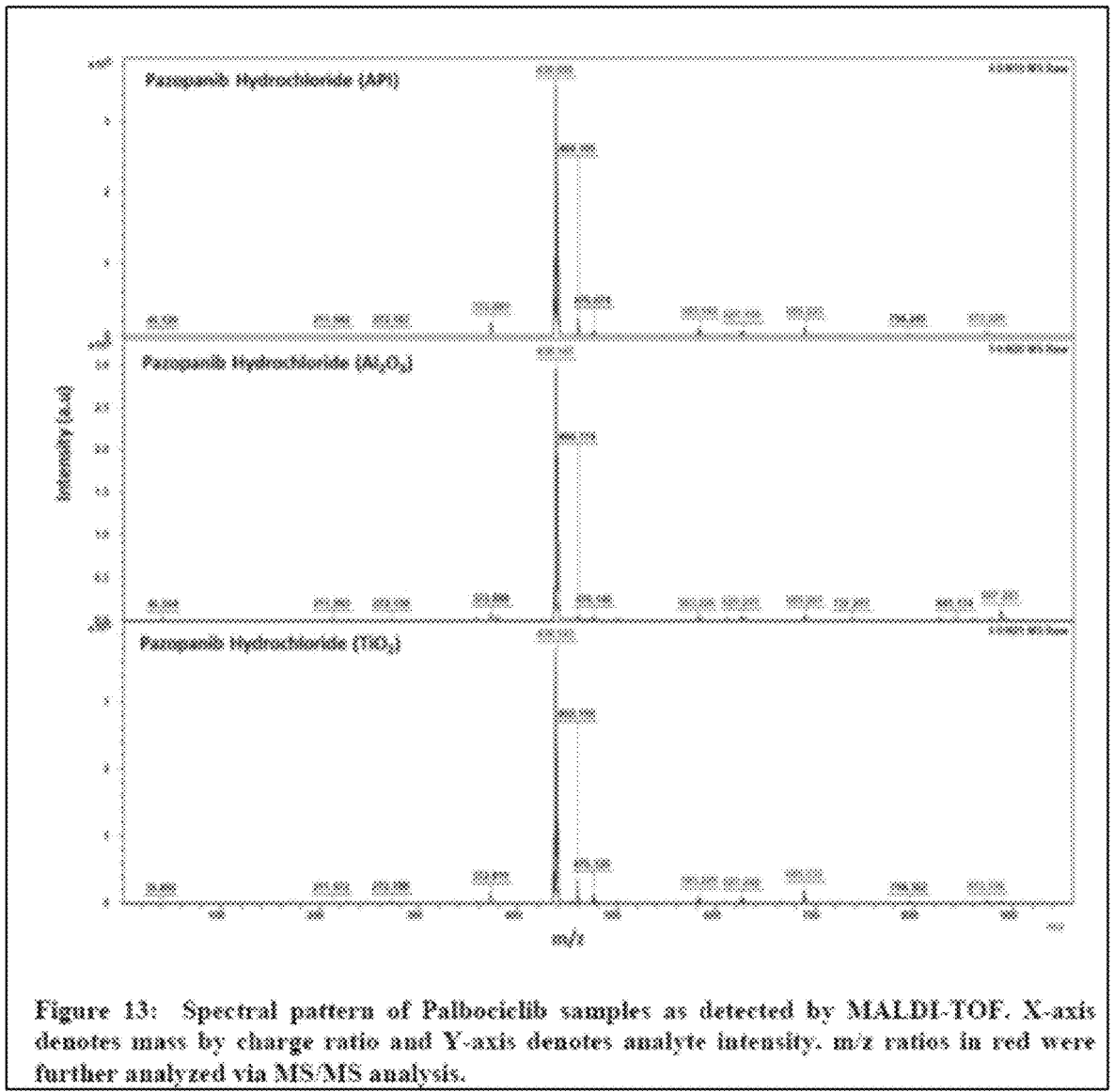
FIG. 8 are graphs depicting the spectral pattern analyzed by MALDI-TOF of pazopanib HCl from compositions of pazopanib HCl uncoated, pazopanib HCl coated with aluminum oxide, or pazopanib HCl coated with titanium oxide.
Figure 9:
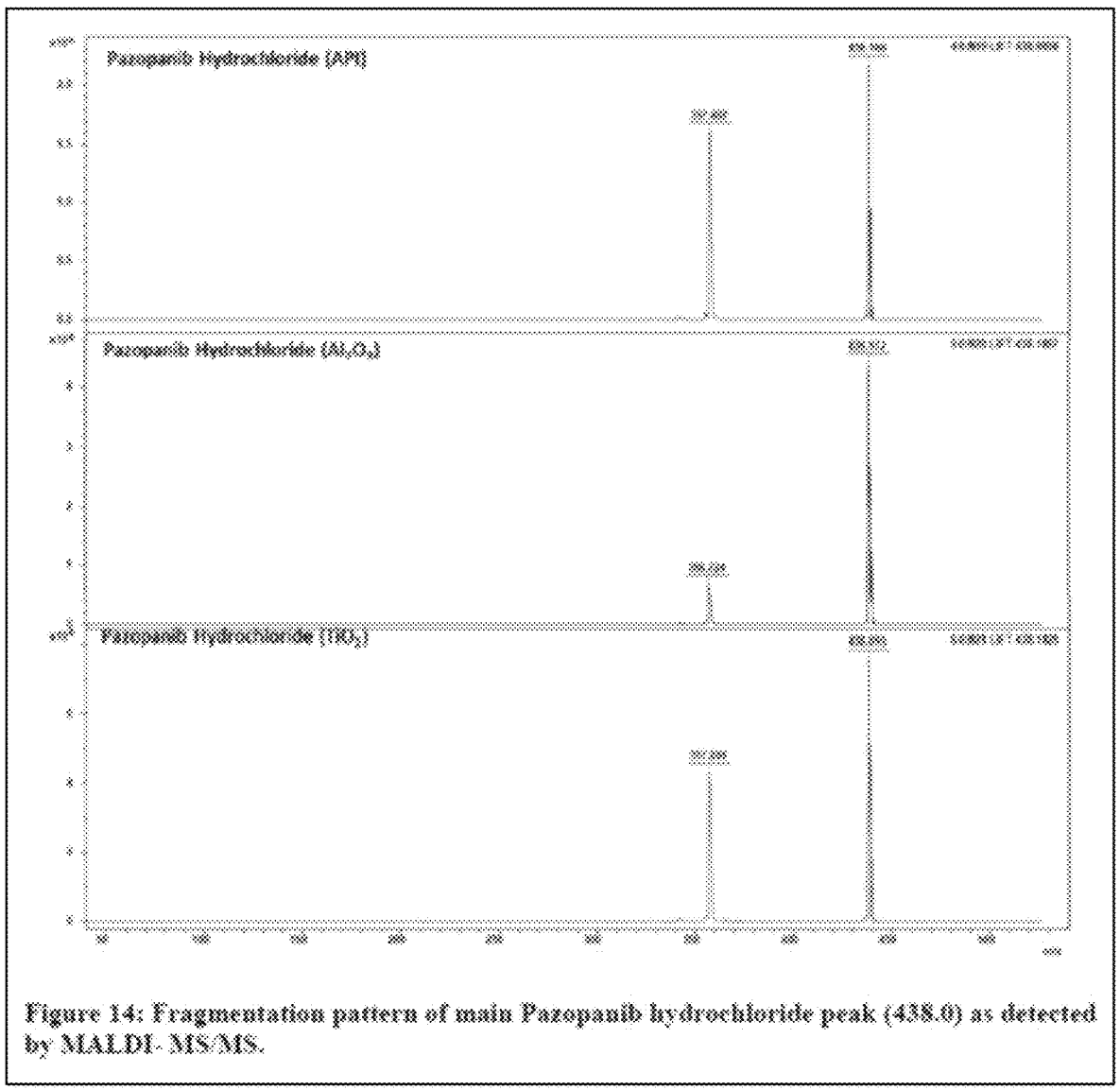
FIG. 9 are graphs depicting the fragmentation pattern analyzed by MALDI MS/MS of pazopanib HCl from compositions of pazopanib HCl uncoated, pazopanib HCl coated with aluminum oxide, or pazopanib HCl coated with titanium oxide.
Figure 10:
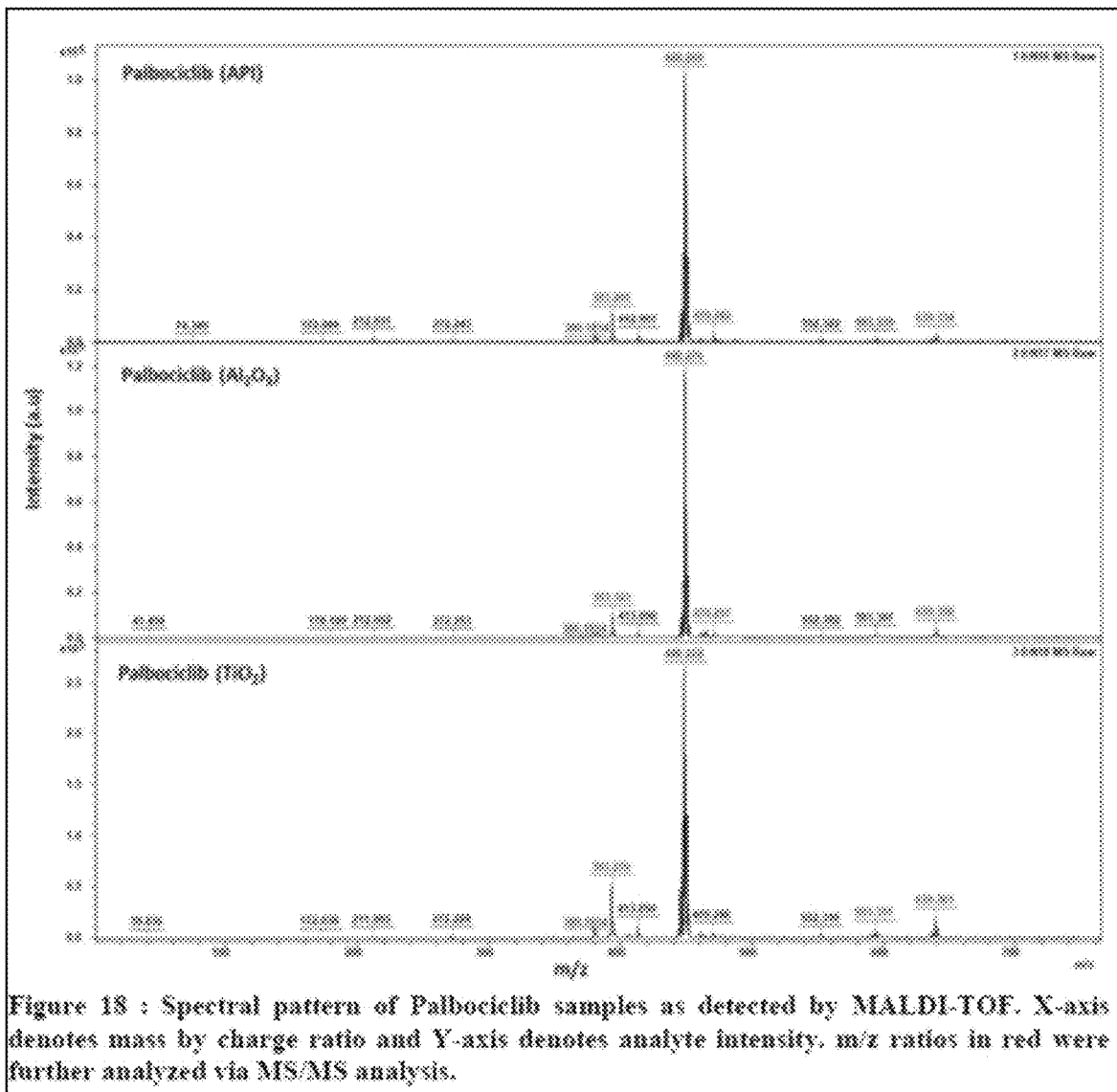
FIG. 10 are graphs depicting the spectral pattern analyzed by MALDI-TOF of palbociclib from compositions of palbociclib uncoated, palbociclib coated with aluminum oxide, or palbociclib coated with titanium oxide.
Figure 11:
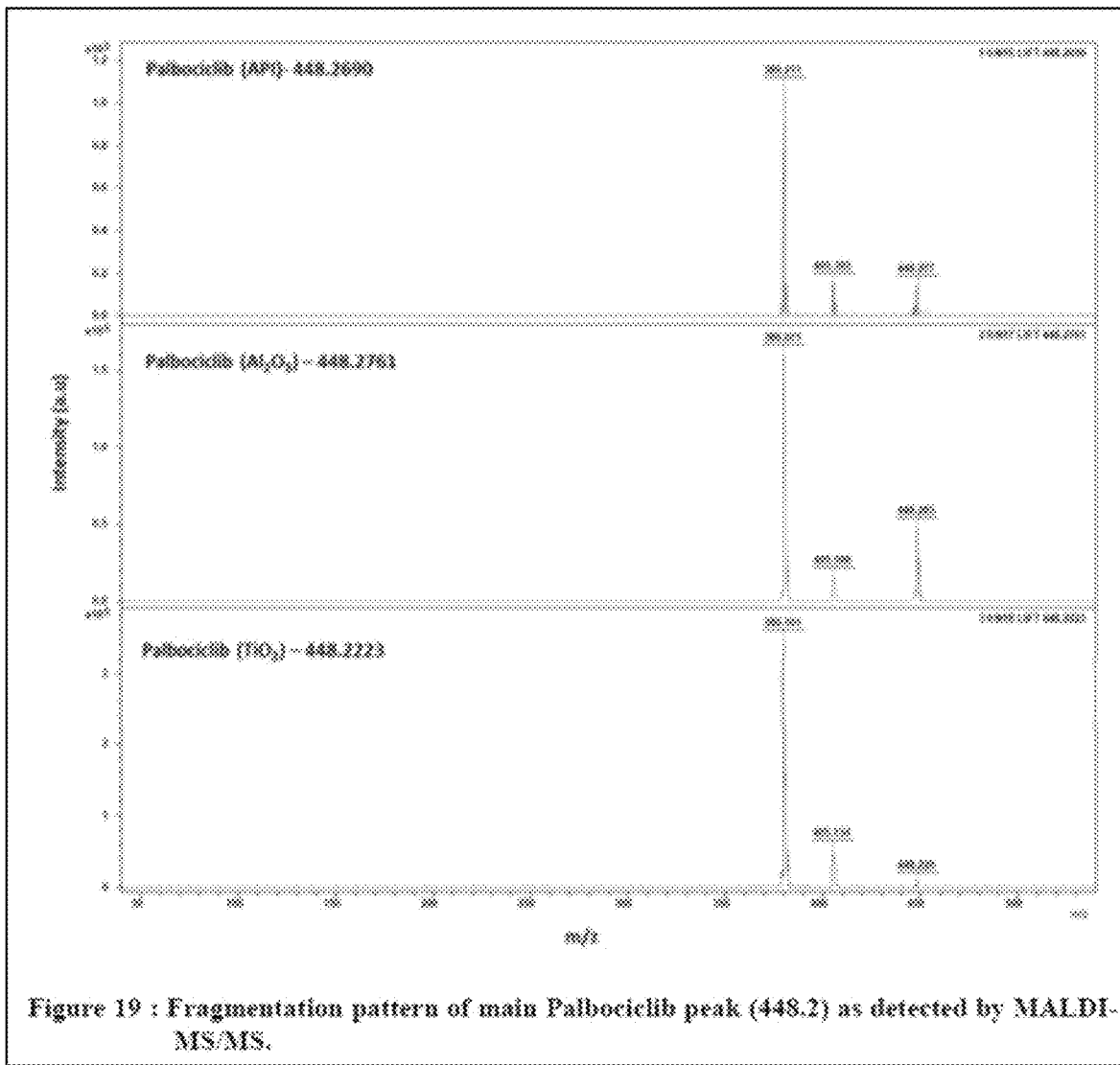
FIG. 11 are graphs depicting the fragmentation pattern analyzed by MALDI MS/MS of palbociclib from compositions of palbociclib uncoated, palbociclib coated with aluminum oxide, or palbociclib coated with titanium oxide.
Figure 12:
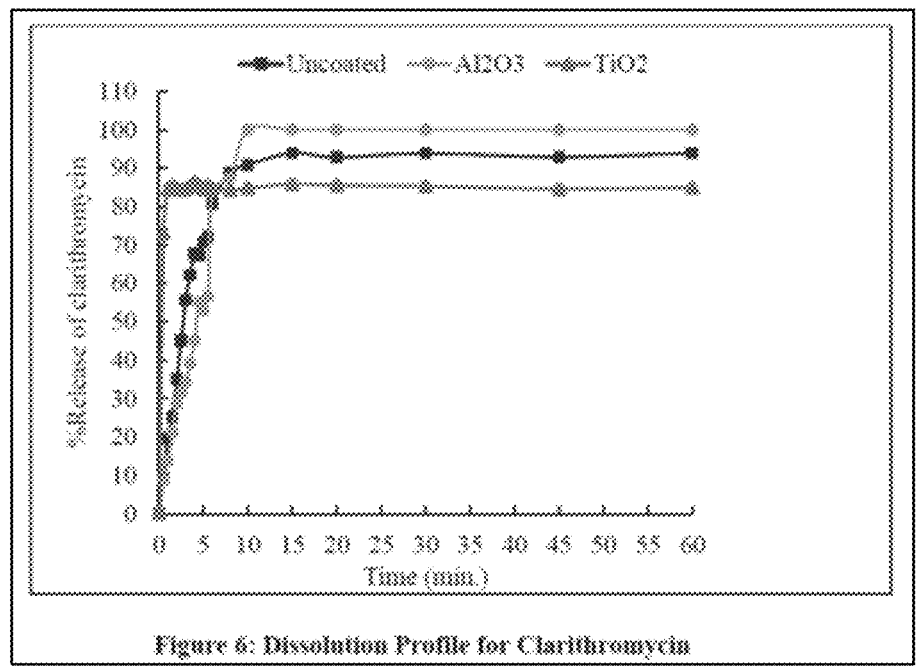
FIG. 12 is a graph showing relative percentage release over time of clarithromycin from clarithromycin uncoated, clarithromycin coated with aluminum oxide, or clarithromycin coated with titanium oxide analyzed by UV spectroscopy.
Figure 13:
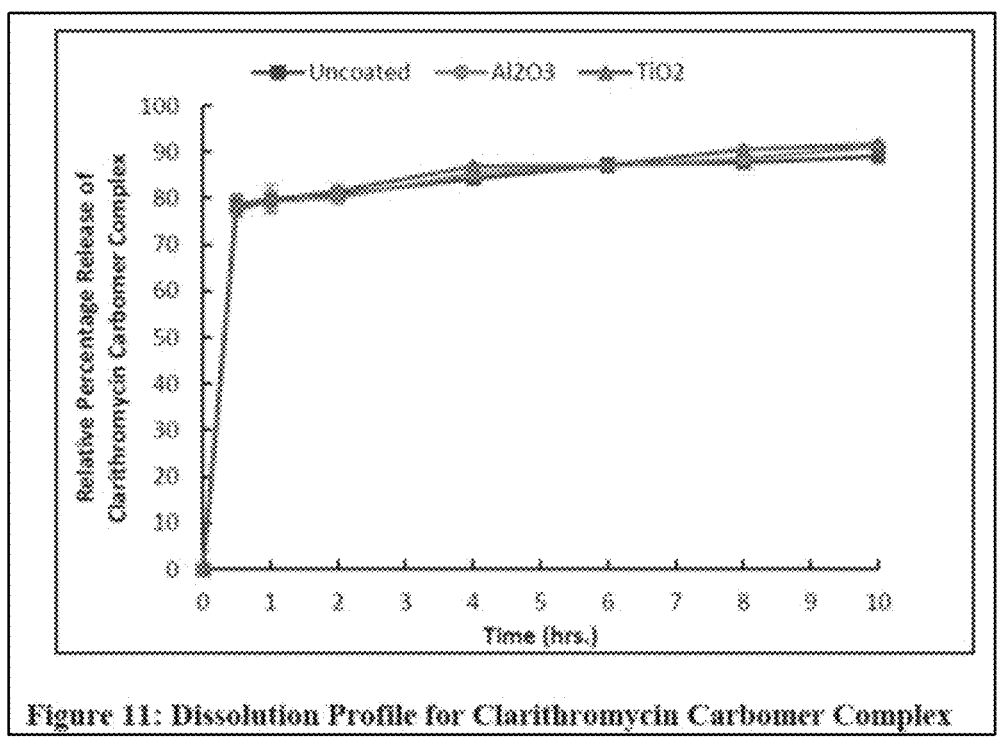
FIG. 13 is a graph showing relative percentage release over time of clarithromycin carbomer complex (CCC) from CCC uncoated, CCC coated with aluminum oxide, or CCC coated with titanium oxide analyzed by UV spectroscopy.
Figure 14:
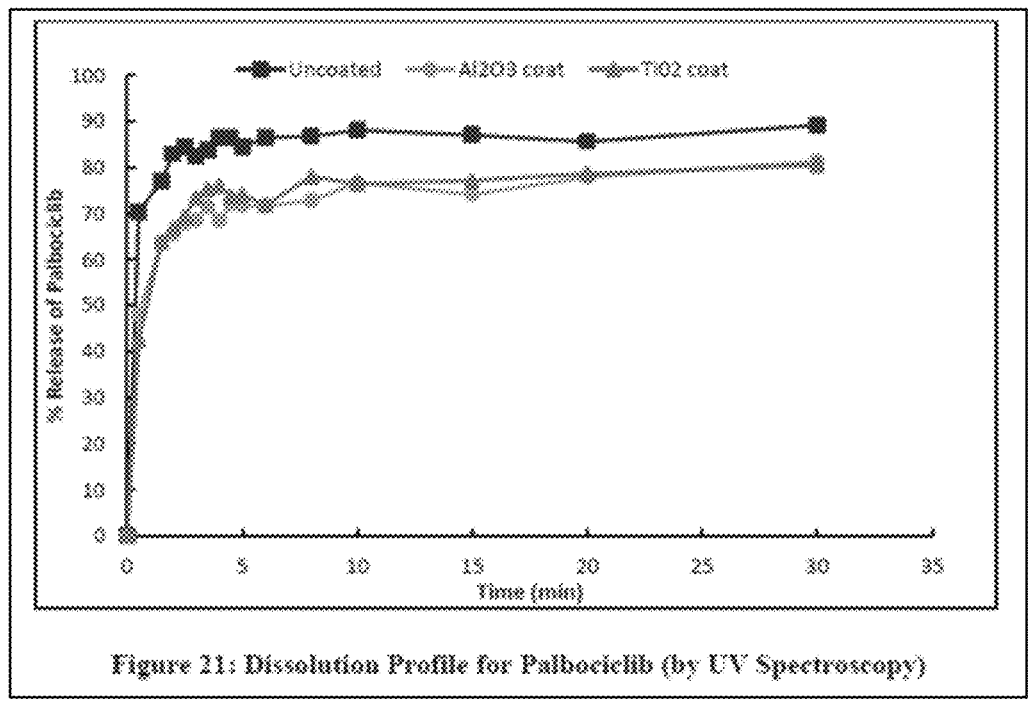
FIG. 14 is a graph showing relative percentage release over time of palbociclib from palbociclib uncoated, palbociclib coated with aluminum oxide, or palbociclib coated with titanium oxide analyzed by UV spectroscopy.

Results
FIG. 3 shows representative residual gas analysis traces measuring during steps (d), (h), (i), and (m) for one cycle of the method. This method reproducibly shows growth rates between 2 and 4 angstroms of metal oxide coating per cycle. In contrast, a different method that limits growth to ALD only exhibited average growth per cycle of 1 angstroms per cycle. Without wishing to be bound to a particular theory, given the observed growth rate for this method the growth may be mediated by a combination of ALD and CVD.

Example 2: Determine if Encapsulation of Small Molecules by Metal Oxide Coatings Alters Structure or the Dissolution Profile To evaluate if encapsulation of small molecules by metal oxide coatings altered structure or the dissolution profile, the small molecules clarithromycin, clarithromycin carbomer complex, pazopanib HCl. palbociclib, and amoxicillin potassium clavulanate were encapsulated by metal oxide coatings and the resulting particles were subjected to chemical analysis to determine if the metal oxide coatings altered the structure or dissolution profile. The small molecules, in powdered form, were encapsulated by the methods provided in the present disclosure with the following modifications shown in the Table below.

| Small Molecule | Metal Oxide Material | Number of times the sequential cycles prior to admixing the coated particles with a pharmaceutically acceptable diluent or carrier were repeated |
| --- | --- | --- |
| Clarithromycin | Titanium Oxide | 99 |
| Clarithromycin | Aluminum Oxide | 49 |
| clarithromycin carbomer complex | Titanium Oxide | 99 |
| clarithromycin carbomer complex | Aluminum Oxide | 49 |
| pazopanib HCl | Titanium Oxide | 99 |
| pazopanib HCl | Aluminum Oxide | 49 |
| Palbociclib | Titanium Oxide | 99 |
| Palbociclib | Aluminum Oxide | 49 |
| amoxicillin potassium clavulanate | Titanium Oxide | 99 |
| amoxicillin potassium clavulanate | Aluminum Oxide | 49 |

Methods
High-Performance Liquid Chromatography
Samples at concentration of 1 mg/mL were prepared by dissolution of analyte in a 50:50 volume:volume mixture of acetonitrile and water and filtered through a 0.45 um filter. Exact conditions of analysis, including mobile phase, column, and oven temperature vary with the analyte under consideration. A typical example of analysis uses a mobile phase consisting of 0.05 M pH 4 phosphate buffer mixed with acetonitrile (90:10 v/v), an Agilent Pursuit XRs 3 C-18 3 um column, an oven temperature of 37 C, a flow rate of 0.9 mL/min, an injection volume of 35 uL, and a run time of 5 minutes, with a UV detector at 214 nm.

Matrix-Assisted Laser Desorption/Ionization Coupled to Mass Spectrometry (MALDI-MS)

Samples were prepared by dissolution in a water-acetonitrile mixture in the ratio of 18:82 v/v. Samples were then mixed with a cyano-4-hydroxy-cinnamic acid matrix and loaded onto the MALDI chip. MS data acquisition was performed in the reflectron positive mode.

Results

Results are shown in FIGS. 4-14. The small molecules clarithromycin and clarithromycin carbomer complex coated with either titanium oxide or aluminum oxide compared to uncoated controls exhibited little to no changes in structure as detected by HPLC analysis. The small molecules pazopanib HCl. and palbociclib coated with either titanium oxide or aluminum oxide compared to uncoated controls exhibited little to no changes in structure as detected by MALDI-MS analysis. The small molecules clarithromycin, clarithromycin carbomer complex, and palbociclib coated with either titanium oxide or aluminum oxide and pazopanib HCl coated with aluminum oxide compared to uncoated controls exhibited little to no changes in dissolution profile. In contrast, the small molecules pazopanib HCl coated with titanium oxide and amoxicillin potassium clavulanate coated with either titanium oxide or aluminum oxide compared to uncoated controls exhibited altered dissolution profiles. Pazopanib HCl coated with titanium oxide exhibits altered dissolution profile—similar initial release and then slowed release—compared to uncoated controls. Amoxicillin potassium clavulanate coated with titanium oxide exhibits altered dissolution profile—slower initial release and then fast release with no saturation of release by 30 min—compared to uncoated controls. Finally, amoxicillin potassium clavulanate coated with aluminum oxide exhibits altered dissolution profile—slower initial release, then fast release—compared to uncoated controls.

Conclusion:

This Example demonstrates that encapsulation of five small molecules by either titanium oxide or aluminum oxide does not confer significant decreases to small molecule structure, but can confer either little to no change or a significant change to dissolution profiles depending on the small molecule and/or the metal oxide coating. Without wishing to bound to particular theory, Applicants note that taken as a whole, it is surprising that 1) the effect on dissolution profile can vary so widely for the same coating material (based on process conditions, API, and dissolution conditions); and 2) coatings made from the same basic materials can also have essentially no impact on dissolution profile. This implies a versatile process that can produce dissolution profiles tailored to specific applications using the same basic materials. Applicants conclude a skilled practitioner could test different methods or parameters, as described herein, to generate small molecules coated with select metal coatings that do not have significantly reduced structure and either do or do not exhibit altered dissolution profiles compared to uncoated small molecules.

Example 3: Determine if Encapsulation of Small Molecules by Metal Oxide Coatings Slows Crystallization of Amorphous Indomethacin Exposed to Moisture To evaluate if encapsulation of small molecules by metal oxide coatings altered structure or the dissolution profile, the small molecule indomethacin was encapsulated by metal oxide coatings and the resulting particles were subjected to chemical analysis to determine if the metal oxide coatings altered crystallinity of amorphous indomethacin. The small molecules, in powdered form, were encapsulated by the methods provided in the present disclosure with the following modifications shown in the Table below.

| Small Molecule | Metal Oxide Material | Thickness of metal oxide material coating |
|---|---|---|
| indomethacin | Titanium Oxide | ~10 nm |
| indomethacin | Aluminum Oxide | ~10 nm |

Methods

Assessment of Crystallinity of Amorphous Indomethacin

Amorphous indomethacin was prepared by freeze drying of standard indomethacin samples and crystalline content before and after exposure to moisture was measured by differential scanning calorimetry (DSC). The area under the crystallization peak was used to determine the specific heat of crystallization for the amorphous materials. The percent crystallinity for partially crystalline materials was determined by dividing the heat of crystallization for the partially crystalline material by the heat of crystallization for the fully amorphous material, subtracting the value from 1, and multiplying by 100.

Results

Figure 15:
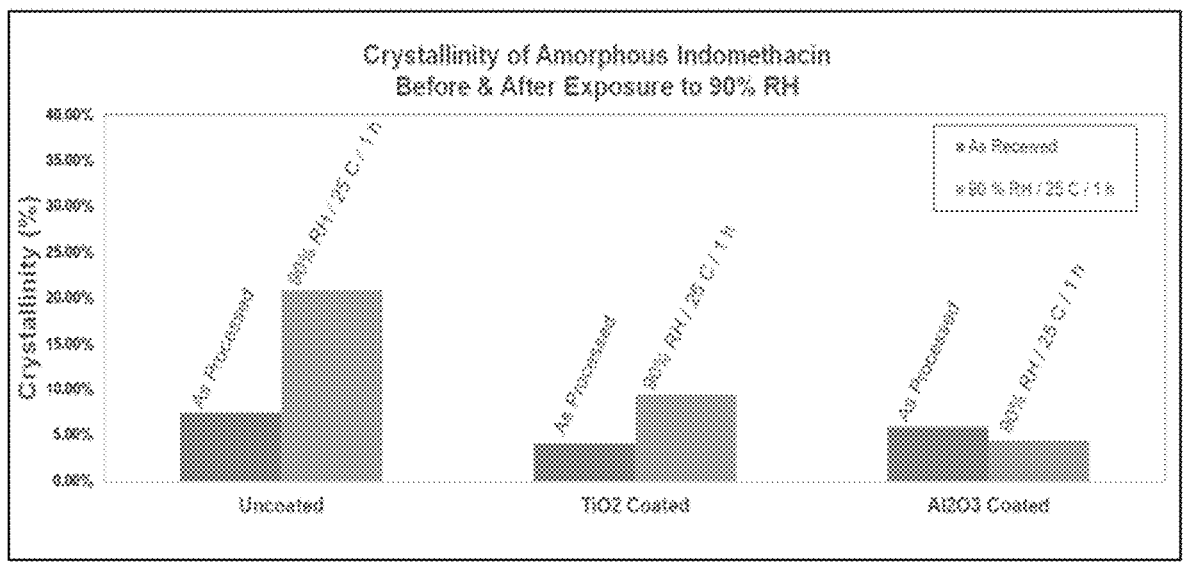
FIG. 15 is a graph showing crystallinity percentage of compositions comprising indomethacin uncoated, indomethacin coated with aluminum oxide, or indomethacin coated with titanium oxide plus and minus exposure to 90% relative humidity.

The small molecule indomethacin coated with either titanium oxide or aluminum oxide compared to uncoated controls exhibited reduced conversion to crystalline state from amorphous state in as processed state and after exposure to 90% relative humidity (RH) (FIG. 15).

Conclusion:

The present Example provides guidance that the provided methods can generate small molecules coated with metal oxide materials that are more stable, specifically such that the drug in the coated particles exhibits reduced conversion to crystalline state from amorphous state in as processed state and after exposure to stress—e.g., 90% RH.

Example 4: Determine if Provided Methods Enable Uniform, Conformal, and Thin Metal Oxide Coatings on Small Molecules To evaluate if provided methods enable uniform, conformal, and thin metal oxide coatings on small molecules, acetaminophen was coated with metal oxide material by methods in the present disclosure and analyzed by atomic layer microscopy and XPS analysis. The small molecules, in powdered form, were encapsulated by the methods provided in the present disclosure.

Methods

Transmission Electron Microscopy

The TEM-ready sample was prepared using the in situ FIB lift out technique on an FEI Strata 400 Dual Beam FIB/SEM. The sample was capped with protective carbon and e-Pt/I-Pt prior to milling. The TEM lamella thickness was ~100 nm. The sample was imaged with a FEI Tecnai TF-20 FEG/TEM operated at 200 kV in bright-field (BF) TEM mode and high-resolution (HR) TEM mode. Energy dispersive spectroscopy (EDS) was used to obtain qualitative elemental maps of the images.

XPS Analysis

Figure 16:
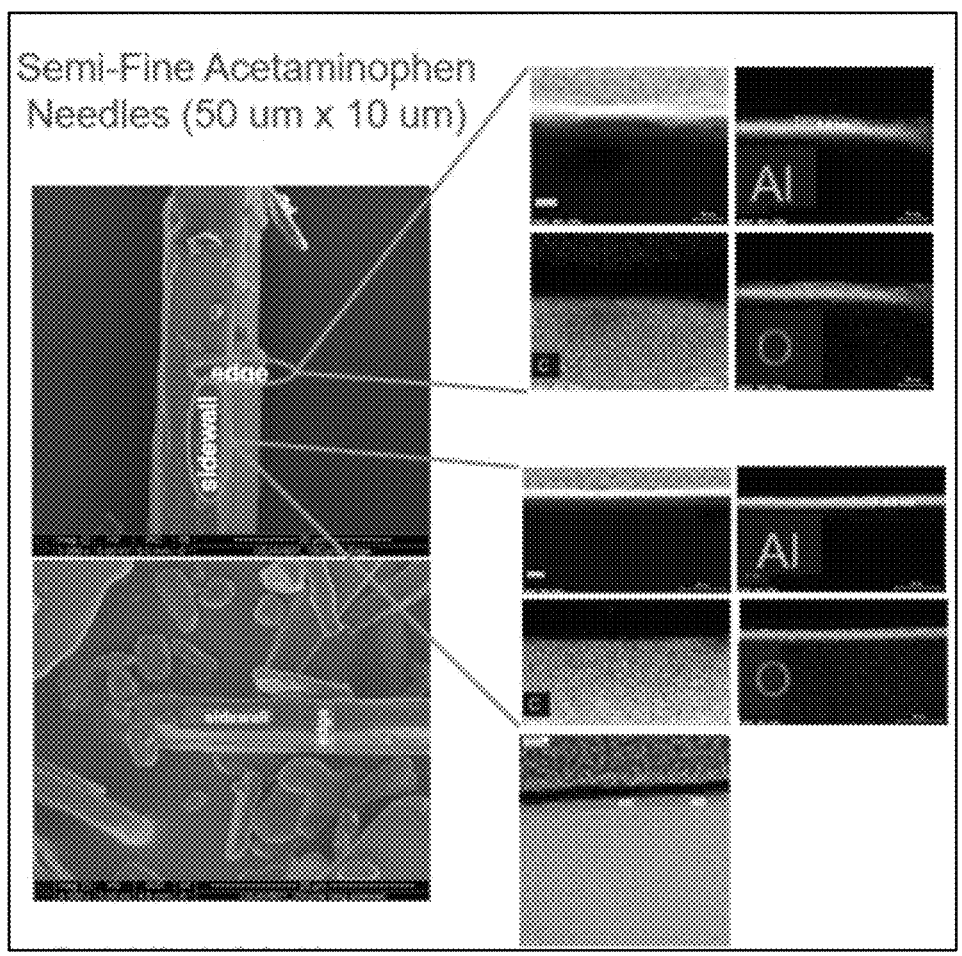
FIG. 16 are representative images acquired by transmission electron microscopy of acetaminophen coated with metal oxide material.
Figure 17:
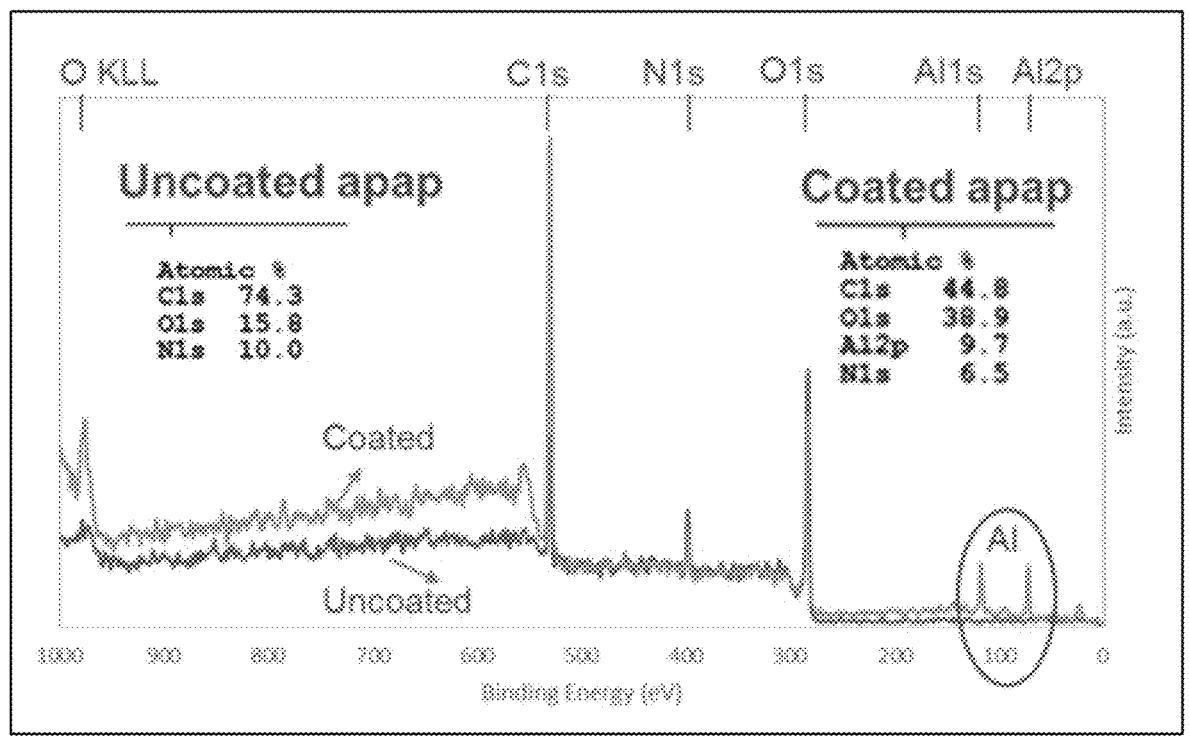
FIG. 17 is a graph showing profiles of intensity versus binding energy for compositions of acetaminophen uncoated or acetaminophen coated with metal oxide material as determined by XPS analysis; insets are tables listing the percentages of C1s, O1s, and N1s quantified from the graphs.

X-ray photoelectron spectroscopy (XPS) was performed on the samples to obtain details of the surface chemistry before and after coating. Powdered samples were mounted on an adhesive substrate and loaded into the instrument. Soft x-rays (1486 eV) were used to excite the sample, the x-ray penetration depth was 5 nm, and the spot size was 200 um.
Results Direct TEM imaging of cross-sections prepared by focused ion beam (FIB) milling of coated acetaminophen particles shows uniform, conformal coating of drug particles with aluminum oxide at the nanometer scale regardless of location on the particles (FIG. 16). Energy dispersive spectroscopy (EDS) proved qualitatively that the coatings consist substantially of aluminum and oxygen (FIG. 17).
Conclusion:

The present Example provides guidance that the provided methods do enable uniform, conformal, and thin metal oxide coatings on small molecules with nanometer level precision.

Example 5. Determine if Encapsulation of Lyophilized Monoclonal Antibodies (mAbs) by Metal Oxide Coatings Alters mAb Structure, Stability, or Ability to Bind Target Polypeptides To evaluate if encapsulation of lyophilized mAbs by metal oxide coatings altered mAb structure or stability, the mAbs Trastuzumab (Herceptin®) and Bevacizumab (Avastin®) were encapsulated by metal oxide coatings and the resulting particles were subjected to biochemical and chemical analysis to determine if the metal oxide coatings altered the mAb structure, stability, or ability to bind target polypeptides. The two mAbs were encapsulated by the methods provided in the present disclosure with the following modifications: (1) for Herceptin® the sequential cycles prior to admixing the coated particles with a pharmaceutically acceptable diluent or carrier was performed 99 times and the vaporous or gaseous metal precursor was aluminum oxide ($Al_2O_3$); (2) for Avastin® the sequential cycles prior to admixing the coated particles with a pharmaceutically acceptable diluent or carrier was performed 49 times and the vaporous or gaseous metal precursor was titanium oxide ($TiO_2$)

Methods

Liquid Chromatography Coupled with Mass Spectrometry

Reverse Phase Chromatography (RPC) was performed on AdvanceBio RP mab C4 (Agilent Technologies) column using Agilent 1260 Infinity Bio-inert Quaternary LC system coupled to Agilent 6230 electrospray ionization-time of flight-mass spectrometer (ESITOF-MS) instrument with mobile phase A (0.1% (v/v) FA) and 10% mobile phase B (0.1% (v/v) FA in acetonitrile). Samples were buffer exchanged through 10 kDa MWCO centricons (Pall Corporation), loaded on the column and separated using a linear gradient from 10%-65% B at a flow rate of 0.5 ml/min. MS spectra was calibrated in positive ion mode and TIC recorded for 1,000-7,000 m/z. The capillary gas temperature/voltage (Vcap) was set to 350° C./5,500 V, respectively and the fragmentor voltage (Vfrag) was 400 V. The MS spectra was deconvoluted using the maximum entropy (MaxEnt) algorithm as part of the Agilent MassHunter Qualitative Analysis and BioConfirm software.

Peptide Mapping

Reverse phase Chromatography (RPC) was performed on AdvanceBio peptide mapping C18 (Agilent Technologies) column operated at 55° C. using Agilent 1260 Infinity Bio-inert Quaternary LC system coupled to an Agilent 6230 ESI-TOF-MS instrument with mobile phase A (0.1% (v/v) TFA) and mobile phase B (0.1% (v/v) TFA in acetonitrile). Digested samples were injected on the column and separated using a linear gradient from 5%-65% B at a flow rate of 0.3 ml/min. MS spectra was calibrated in positive ion mode and TIC recorded for 100-3200 m/z. The capillary gas temperature/Vcap was set to 300° C./4500 V, respectively and the Vfrag was 300 V. MS spectrum was analyzed using the protein molecular feature extraction (MFE) algorithm in the Agilent MassHunter Qualitative Analysis and BioConfirm software to obtain list of probable peptides and matched with in-silico digested mAb peptides to get the sequence coverage.

Fourier Transform Infrared Spectroscopy (FTIR)

FTIR spectra were recorded using the attenuated total reflection (ATR) method at room temperature. FTIR absorbance spectra of 0.5 mg/ml of mAb was collected in the range of 500-4000 $cm^{-1}$. The second derivative spectra was obtained by applying an 11 point Savitzky-olay smoothing of original spectra. The second derivative spectra in the range of $1600^{-}700$ $cm^{-1}$ was deconvoluted by the curve-fitting method with the Levenberg-Marquardt algorithm and the peaks corresponding to α-helix (1660-1654 $cm^{-1}$), β-sheet (1637-1614 $cm^{-1}$), turn (1678-1670 $cm^{-1}$), random coil (1648-1638 $cm^{-1}$) and β-antiparallel (1691-1680 $cm^{-1}$) were adjusted and the areas were measured with the Gaussian function. The areas of all the component bands assigned to a given conformation were then summed up and divided by the total area.

Circular Dichroism (CD)

Far-UV CD spectra were recorded in the range of 200-250 nm at 25° C. with a spectral band width of 5 nm using 0.1 cm path length quartz cell at a scan speed of 50 nm/min. Sample concentration was kept at 0.2 mg/ml and three spectra were scanned, averaged and finally plotted after subtracting the buffer baseline. Mean residue ellipticity (MRE, deg cm2/dmole) was calculated.

Fluorescence Spectroscopy

Intrinsic fluorescence was measured by exciting the protein solution (0.5 mg/ml) at and 295 nm (for excitation of tryptophan only). Emission spectra were recorded in the range of 300-450 nm. Extrinsic fluorescence intensities of samples (0.5 mg/ml) were recorded with excitation at 380 nm and emission between 400 to 600 nm on fluorescence spectrophotometer using ANS (8-Anilinonaphthalene-1-sulfonic acid) dye. All measurements were performed in triplicates and each spectrum represents the average of three scans.

Size Exclusion Chromatography (SEC-HPLC)

Size Exclusion Chromatography was performed on Superdex 200 column using Dionex Ultimate 3000 UHPLC system (Thermo Scientific) with buffer of 300 mM NaCl, and 0.05% NaN3 at pH 6.8. Detection was performed by monitoring UV absorbance at 280 nm. Peak integration and peak area was determined using the Chromeleon software.

Cation Exchange Chromatography (CEX)

Ion Exchange Chromatography was performed using Dionex Ultimate 3000 RSLC system (Thermo Scientific) with Agilent Bio MAb NP5 Column and buffer of 300 mM NaCl, and 0.05% NaN3 at pH 6.8. Detection was performed by monitoring UV absorbance at 280 nm.

Surface Plasmon Resonance (SPR) FcRn Binding Kinetics Assay

The binding kinetic interactions of different mAb samples to human FcRn receptor were measured using Surface Plasmon Resonance in HBS-EP Buffer (GE Healthcare Life Sciences) on Biacore X100™ (GE Healthcare). Recombinant human FcRn antibody was immobilized and samples were injected in a series of concentrations. Kinetic constants were calculated from the sensorgrams using the 1:1 fit model using BIA Evaluation 2.0.1 software.

Stability Analysis

To determine structural integrity and aggregation of the metal oxide coated mAbs over a period of 10 days at 80° C. the higher order structure of mAbs was measured by Fourier Transform Infrared Spectroscopy analysis (FTIR), the tertiary structure of mAbs was measured by intrinsic and extrinsic fluorescence analysis, and profile of size variants was measured by size exclusion chromatography (SEC). Samples were kept in a dry bath at 80° C. and sampled on set time point for testing. FTIR spectra were recorded using the attenuated total reflection (ATR) method at room temperature. FTIR absorbance spectra of 0.5 mg/ml of mAb was collected in the range of 500-4000 cm.−1 The second derivative spectra was obtained by applying an 11 point Savitzky-Golay smoothing of original spectra. The second derivative spectra in the range of 1600-1700 cm-1 was deconvoluted by the curve-fitting method with the Levenberg-Marquardt algorithm and the peaks corresponding to α-helix (1660-1654 $cm^{-1}$), β-sheet (1637-1614 $cm^{-1}$), turn (1678-1670 $cm^{-1}$), random coil (1648-1638 $cm^{-1}$) and β-antiparallel (1691-1680 $cm^{-1}$) were adjusted and the areas were measured with the Gaussian function. The areas of all the component bands assigned to a given conformation were then summed up and divided by the total area. Intrinsic fluorescence was measured by exciting the protein solution (0.5 mg/ml) at 295 nm (for excitation of tryptophan only) Emission spectra were recorded in the range of 300-450 nm. Extrinsic fluorescence intensities of samples (0.5 mg/ml) were recorded with excitation at 380 nm and emission between 400 to 600 nm on fluorescence spectrophotometer using ANS (8-Anilinonaphthalene-1-sulfonic acid) dye. All measurements were performed in triplicates and each spectrum represents the average of three scans. Size Exclusion Chromatography was performed as described above.

Results

Figure 18:
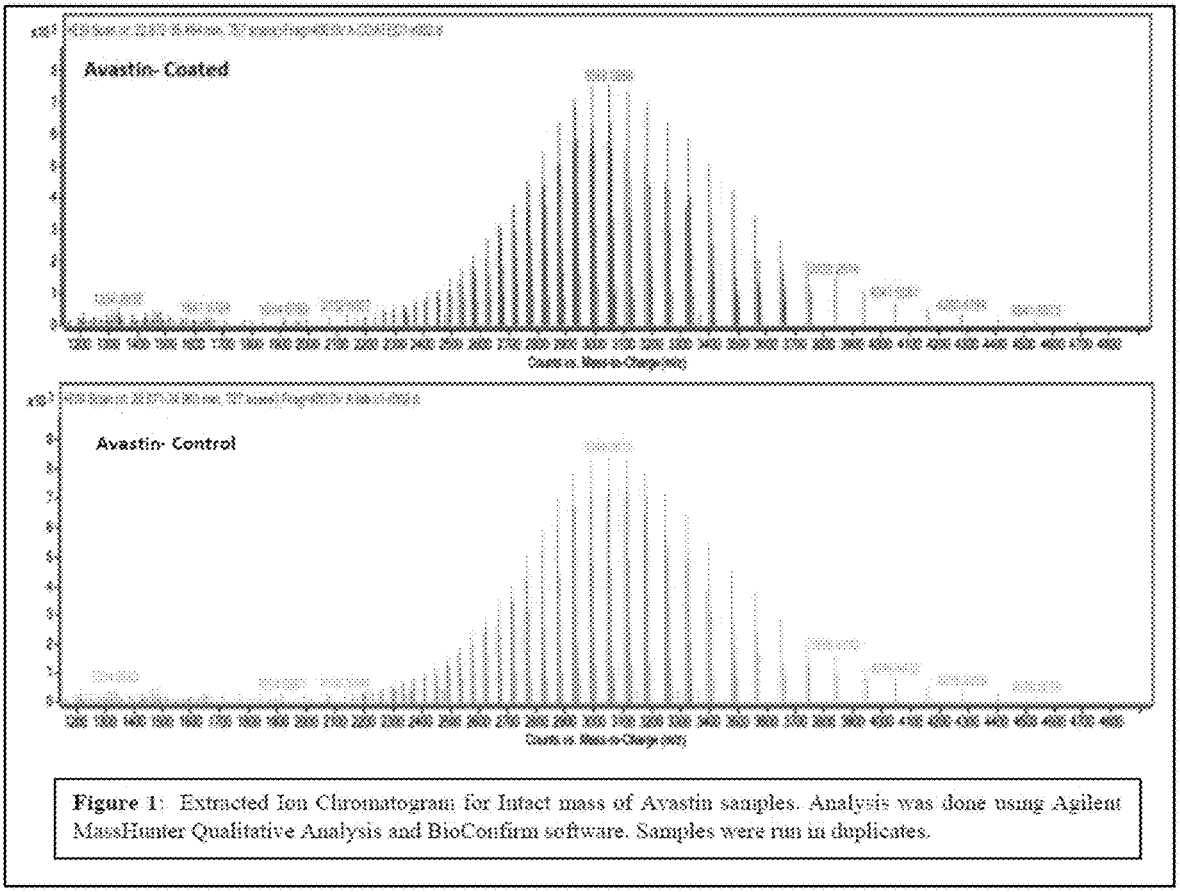
FIG. 18 are graphs showing extracted ion chromatogram for intact mass of Avastin® from compositions of Avastin® uncoated or Avastin® coated with titanium oxide.
Figure 19:
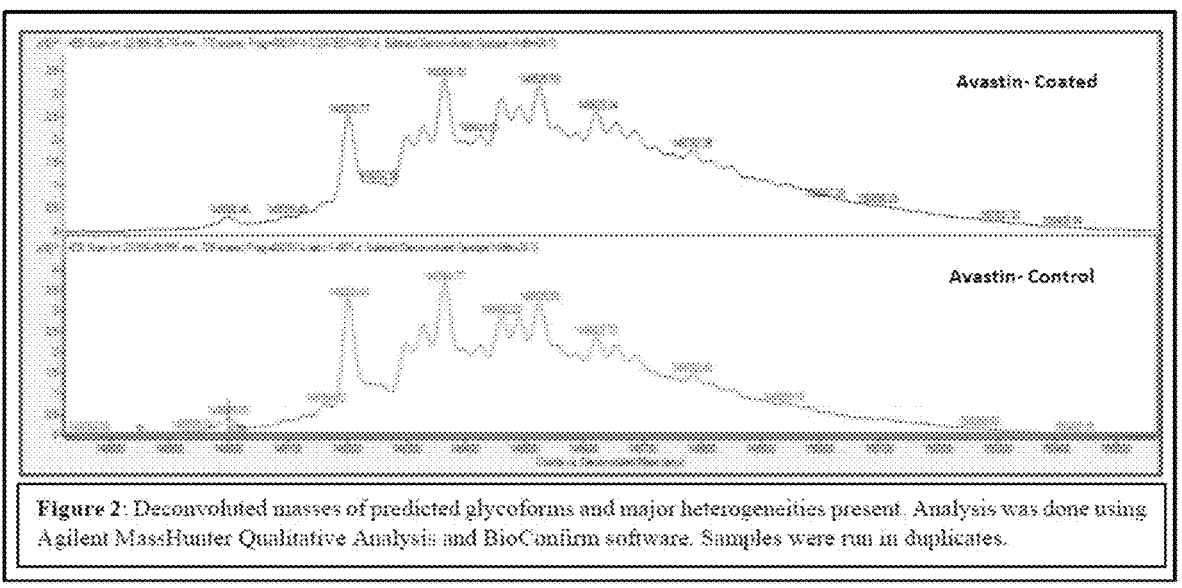
FIG. 19 are graphs showing deconvoluted masses of predicted glycoforms and major heterogeneities detected in compositions of Avastin® uncoated or Avastin® coated with titanium oxide.
Figure 21:
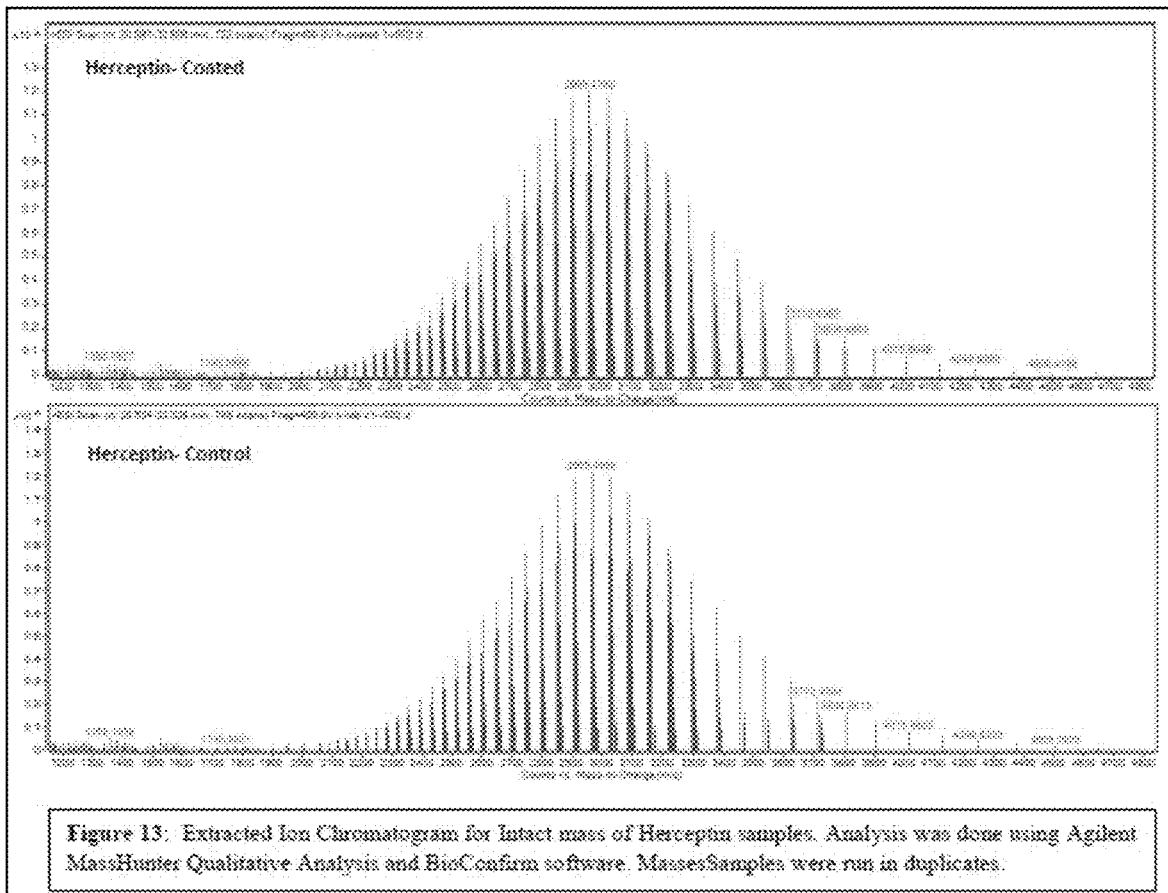
FIG. 21 are graphs showing extracted ion chromatogram for intact mass of Herceptin® from compositions of Herceptin® uncoated or Herceptin® coated with aluminum oxide.
Figure 22:
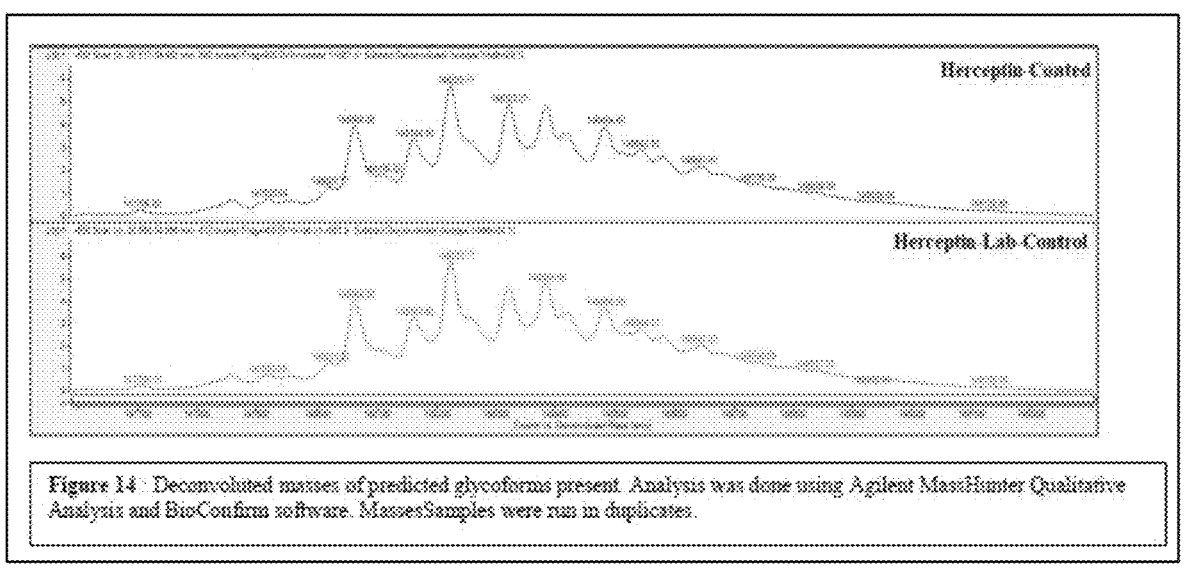
FIG. 22 are graphs showing deconvoluted masses of predicted glycoforms and major heterogeneities detected in compositions of Herceptin® uncoated or Herceptin® coated with aluminum oxide.

To confirm mass and sequence identity of the mAbs encapsulated by the metal coatings, liquid chromatography coupled with mass spectrometry analysis was performed. Results for Avastin® are depicted in FIGS. 18-20. The data suggests that titanium oxide coating has little to no effect on the intact protein mass of Avastin®. The predicted modifications, with exception of one modification, for the coated Avastin® matched those for the uncoated Avastin®. Results for Herceptin® are depicted in FIGS. 21-23. The data suggests that aluminum oxide coating has little to no effect on the intact protein mass of Herceptin® compared to uncoated Avastin®.

Figures 26, 27:
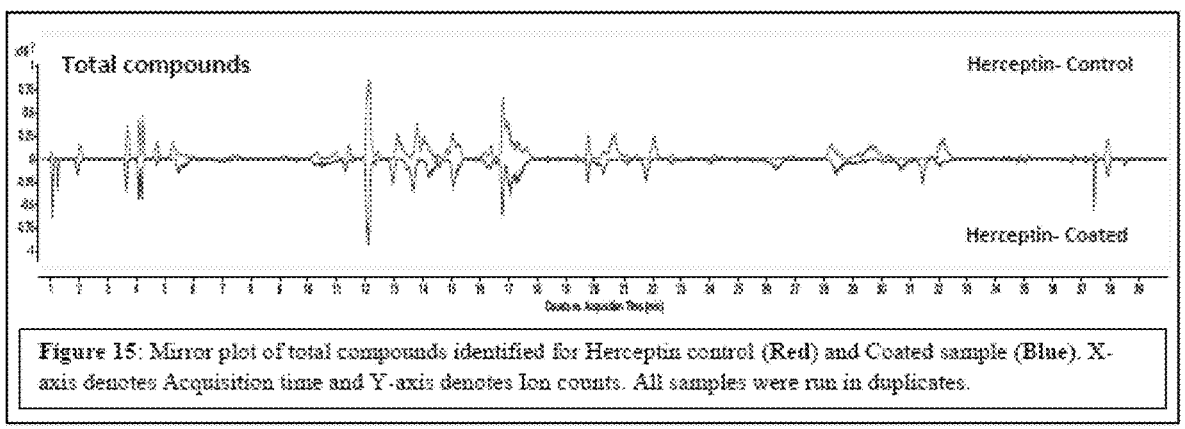
FIG. 26 is a table listing percentage of sequence coverage for double digested compositions of Herceptin® uncoated or Herceptin® coated with aluminum oxide compared to in-silico digested Herceptin® sequence.
FIG. 27 is a plot showing total compounds identified in compositions of Herceptin® uncoated or Herceptin® coated with aluminum oxide.
Figure 28:
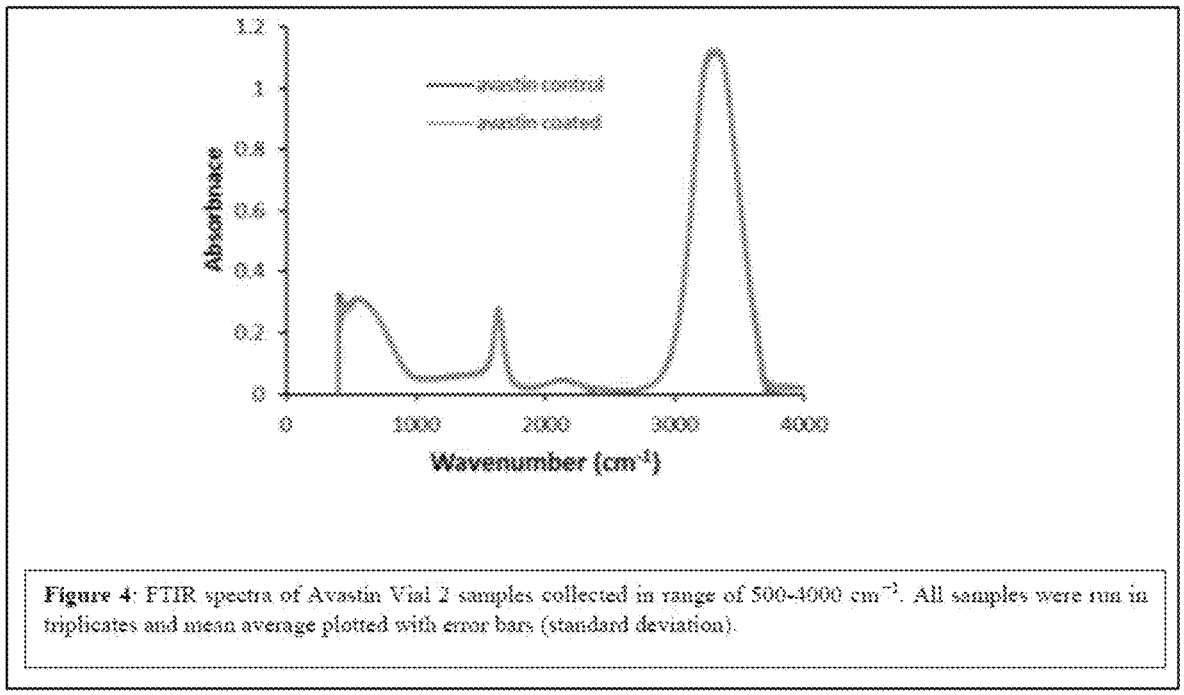
FIG. 28-29 are graphs showing results from FTIR analysis of compositions of Avastin® uncoated or Avastin® coated with titanium oxide.
Figure 29:
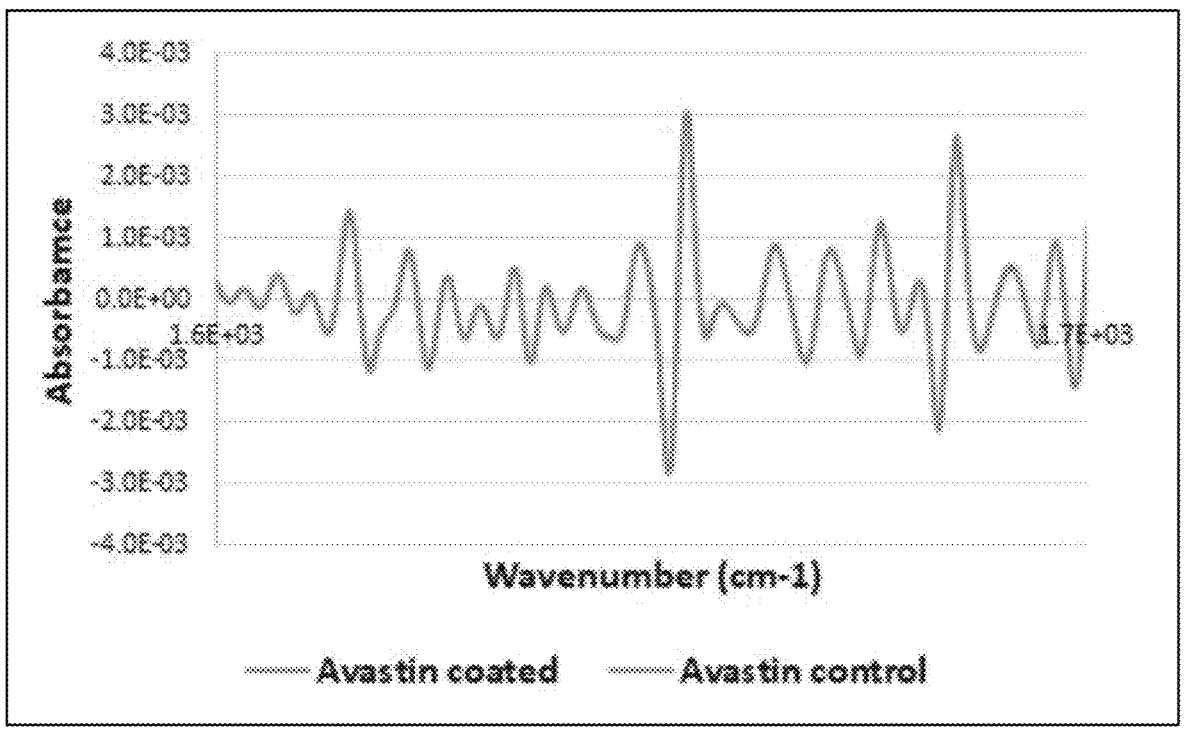
Figure 32:
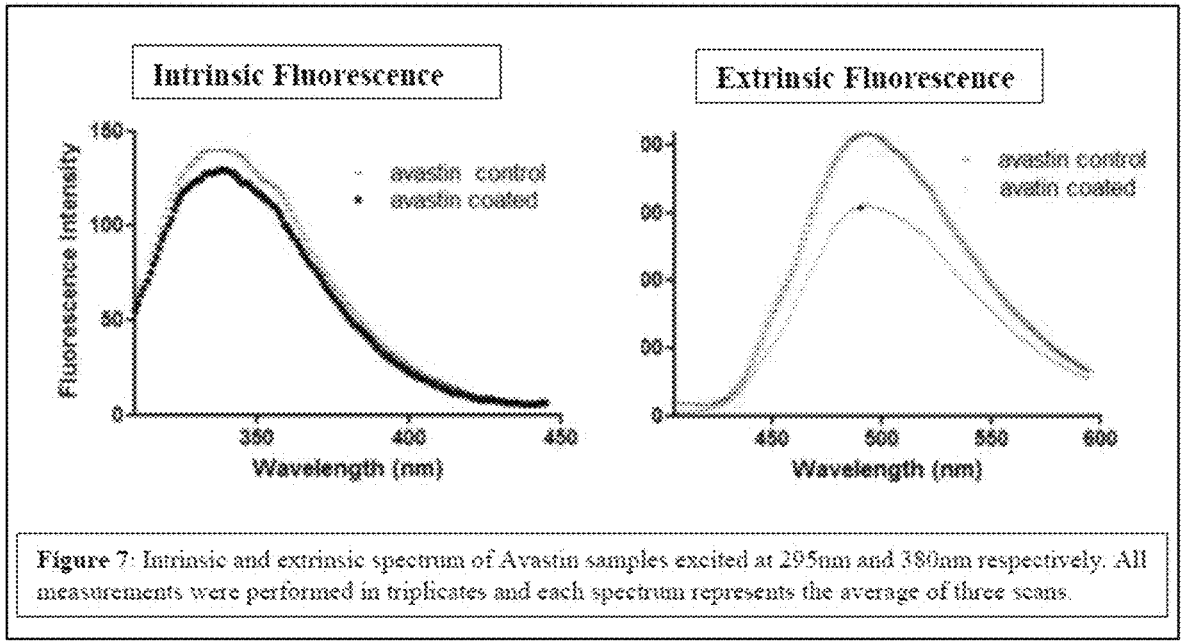
FIG. 32 are graphs showing results of intrinsic and extrinsic fluorescence analysis of compositions of Avastin® uncoated or Avastin® coated with titanium oxide.
Figure 33:
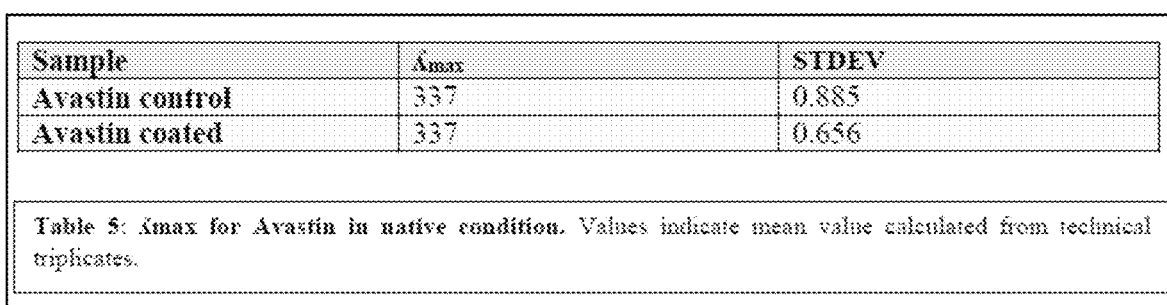
FIG. 33 is a table showing the λmax for compositions of Avastin® uncoated or Avastin® coated with titanium oxide.
Figure 34:
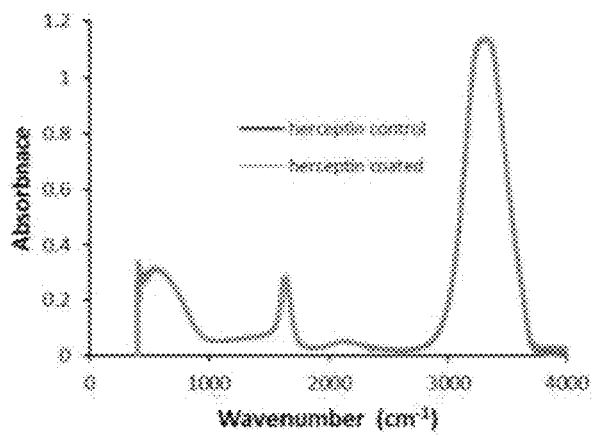
FIG. 34-35 are graphs showing results from FTIR analysis of compositions of Herceptin® uncoated or Herceptin® coated with aluminum oxide.
Figure 35:
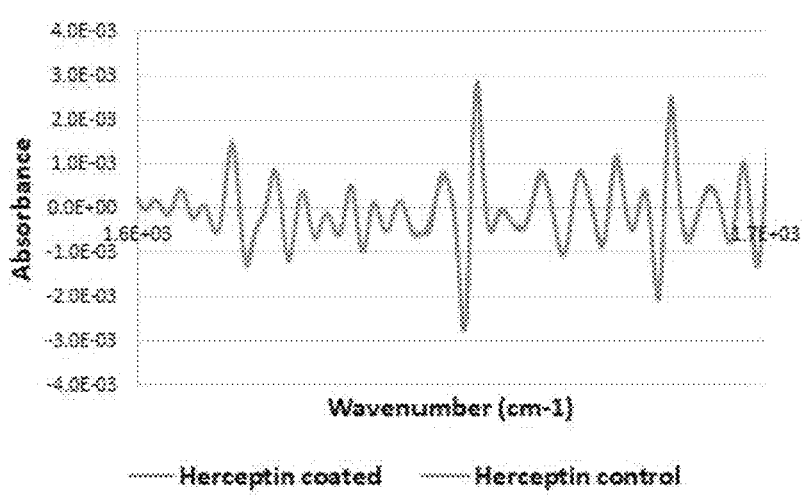
Figure 38:
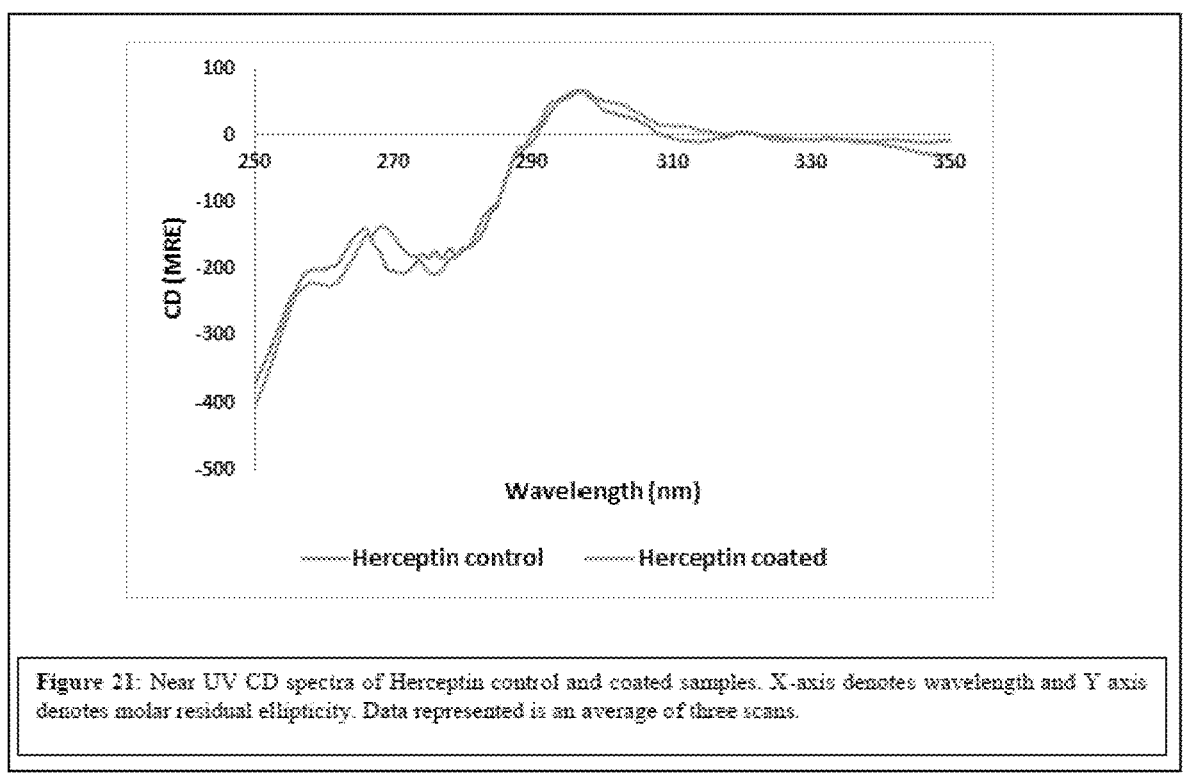
FIG. 38 is a graph showing results of near UV CD analysis of compositions of Herceptin® uncoated or Herceptin® coated with aluminum oxide.

To confirm sequence identify and post-translational modifications of the mAbs encapsulated by the metal coatings, peptide mapping was performed. Results for Avastin® are depicted in FIGS. 24-25. The data suggests that titanium oxide coating has little to no effect on the sequence identity of Avastin® when compared to the in-silico digested Avastin®. Results for Herceptin® are depicted in FIGS. 26-27. The data suggests that aluminum oxide coating has little to no effect on the sequence identity of Herceptin® when compared to the in-silico digested Herceptin®.

Fourier Transform Infrared (FTIR) spectroscopy and circular dichroism (CD) analysis was performed to determine whether there were changes to mAb secondary structure. Fluorescence spectroscopy analysis were performed to determine whether there were changes to mAb tertiary structure. Results for Avastin® are depicted in FIGS. 28-33. The data suggests that titanium oxide coating has little to no effect on the secondary structure of Avastin® compared to uncoated Avastin®. Results for Herceptin® are depicted in FIGS. 34-38. The data suggests that aluminum oxide coating has little to no effect on the secondary structure of Herceptin® compared to uncoated Herceptin® as detected by FTIR. The data suggest that the aluminum oxide has little to no effect on tertiary structure of Herceptin® compared to uncoated Herceptin® as detected by far and near UV circular dichroism analysis.

Figure 39:
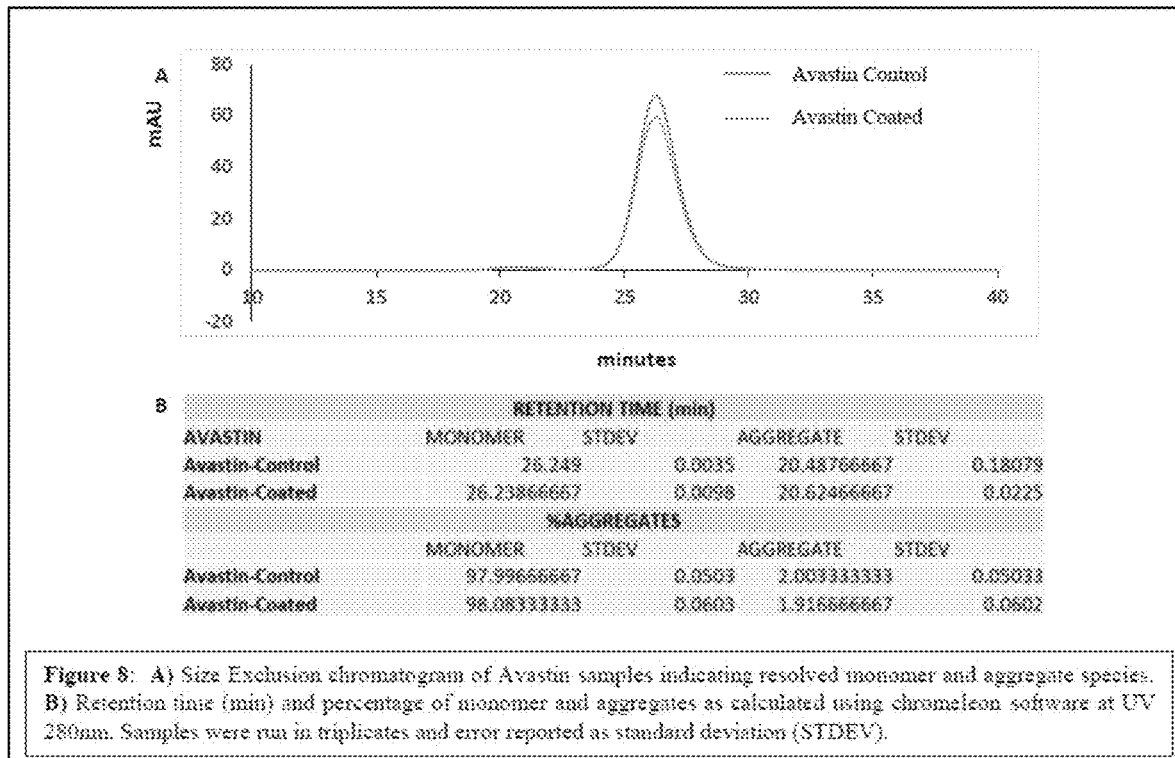
FIG. 39 (Top) is a graph showing results of size exclusion chromatography analysis of compositions of Avastin® uncoated or Avastin® coated with titanium oxide; (Bottom) is a table showing retention times for monomer and aggregate quantified.
Figure 40:
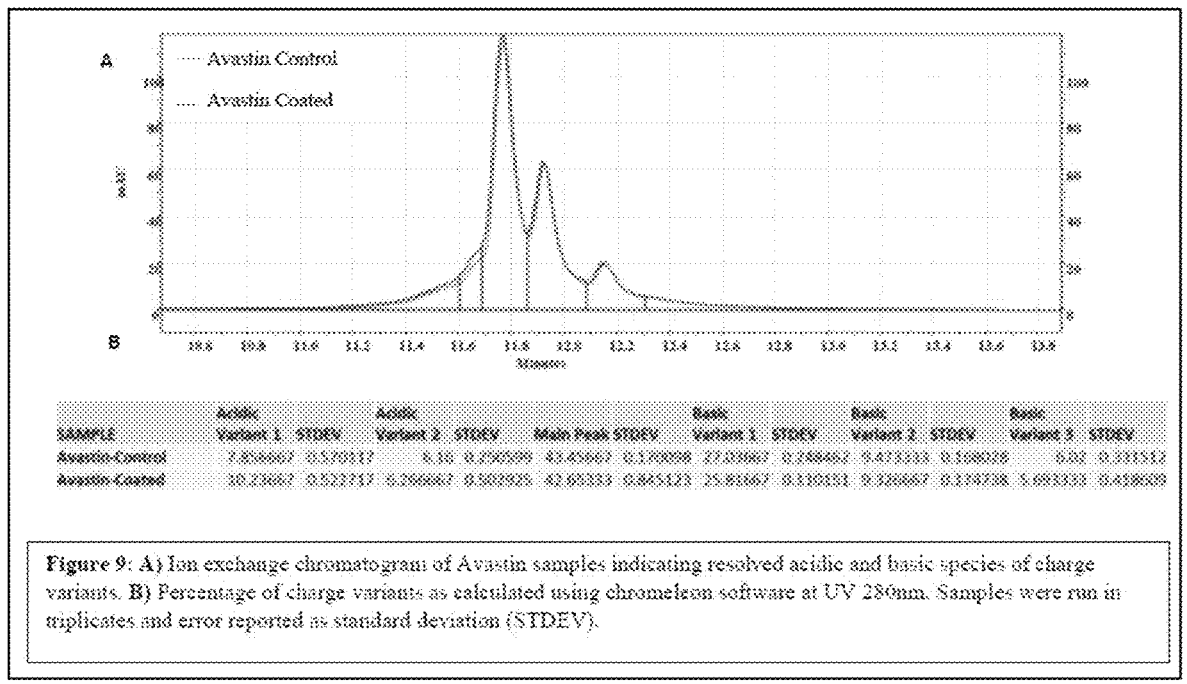
FIG. 40 is a graph showing results of ion exchange chromatography analysis of compositions of Avastin® uncoated or Avastin® coated with titanium oxide FIG. 41 (Top) is a graph showing results of size exclusion chromatography analysis of compositions of Herceptin® uncoated or Herceptin® coated with aluminum oxide; (Bottom) is a table showing retention times for monomer and aggregate quantified.
Figure 41:
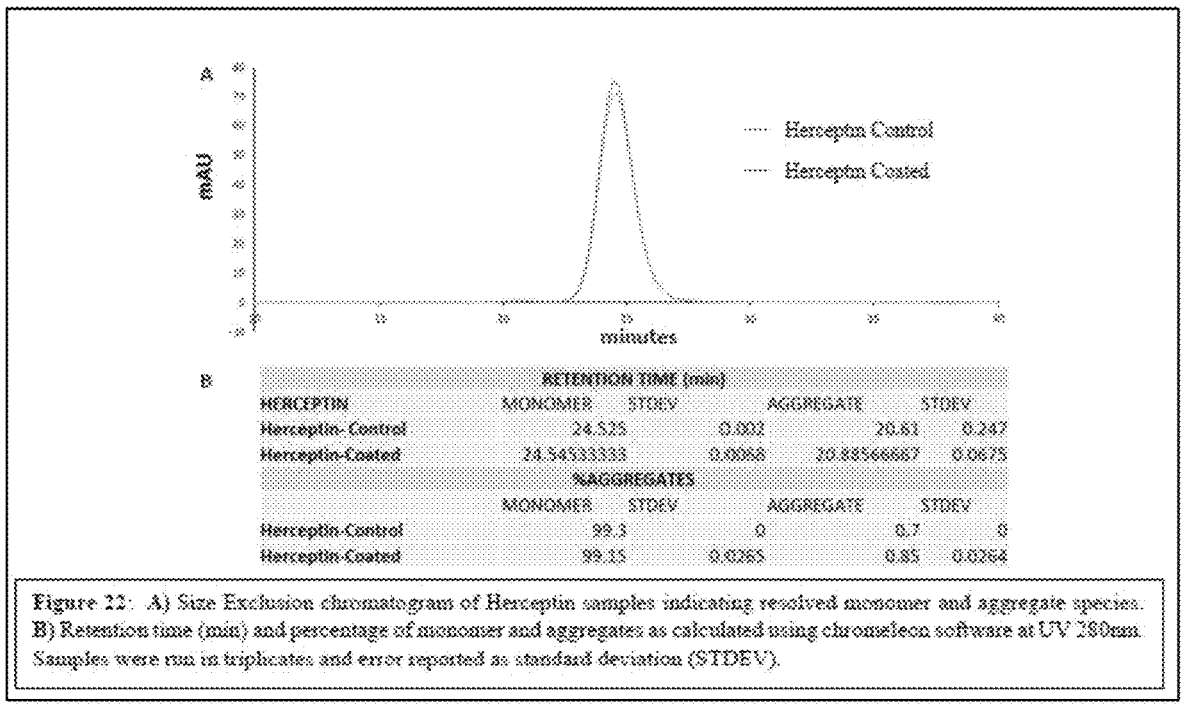
Figure 42:
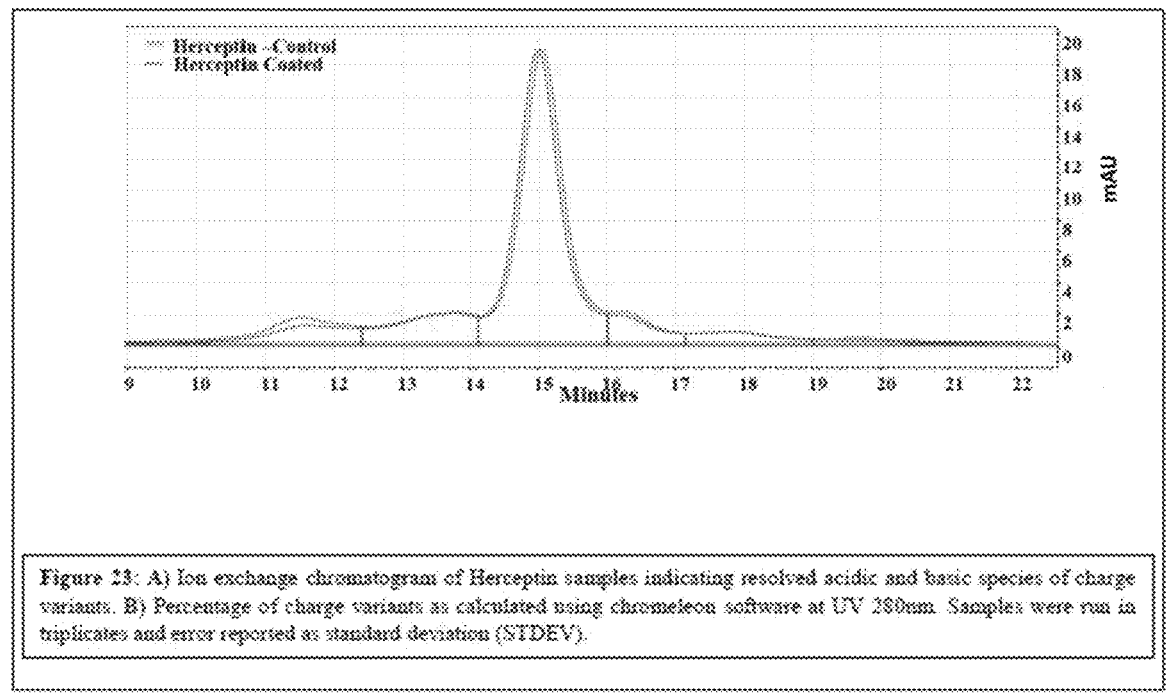
FIG. 42 is a graph showing results of ion exchange chromatography analysis of compositions of Herceptin® uncoated or Herceptin® coated with aluminum oxide.

Size exclusion chromatography (SEC) was performed to determine whether there were changes to size variants in the mAb sample. Cation exchange chromatography (CEX) was performed to determine whether there were changes to charge variant profile in the mAb sample. Results for Avastin® are depicted in FIGS. 39-40. The data suggests that titanium oxide coating has little to no effect on the monomer and aggregate percentage or the percentage of charge variant species of Avastin® compared to uncoated Avastin®. Results for Herceptin® are depicted in FIGS. 40-41. The data suggests that aluminum oxide coating has little to no effect on the monomer and aggregate percentage or the percentage of charge variant species of Herceptin® compared to uncoated Herceptin®.

Figure 43:
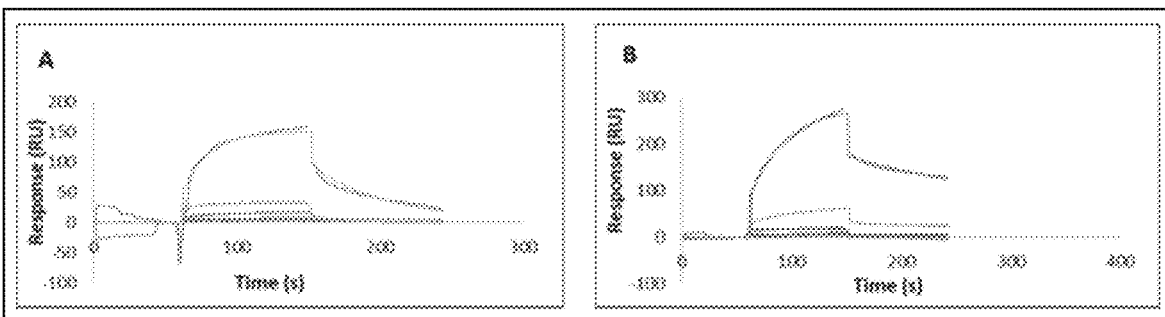
FIG. 43 are graphs showing results of SPR binding assays for Avastin® isolated from compositions of Avastin® uncoated or Avastin® coated with titanium oxide.
Figure 44:
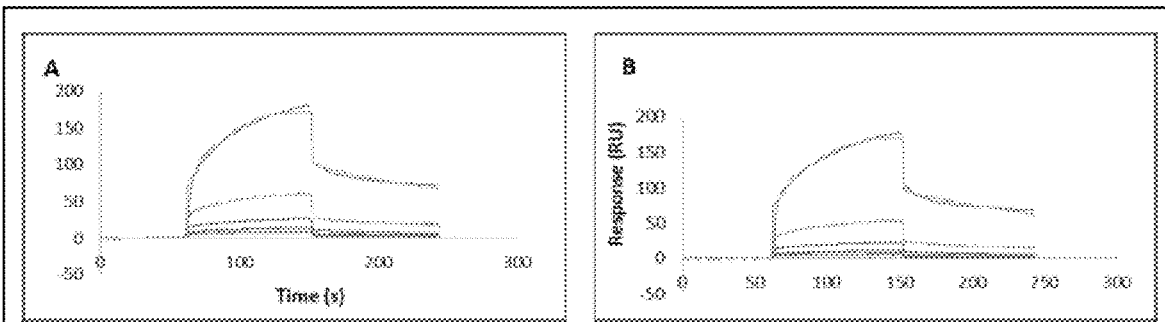
FIG. 44 is a table showing KD values quantified from results shown in FIG. 43.
Figure 45:
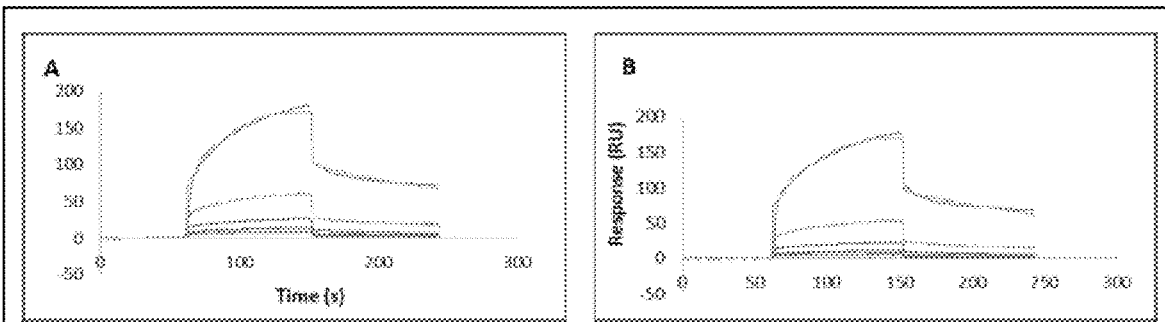
FIG. 45 are graphs showing results of SPR binding assays for Herceptin® isolated from compositions of Herceptin® uncoated or Herceptin® coated with aluminum oxide.
Figures 50, 51:
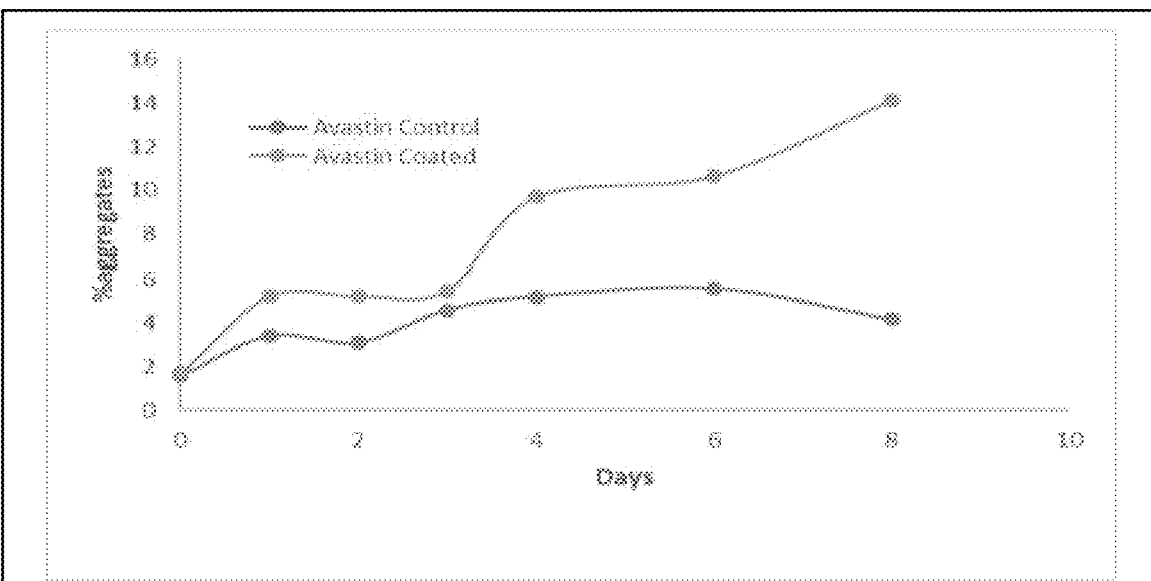
FIG. 50 is a graph showing percentage of aggregates as measured by SEC of Avastin® over time from compositions of Avastin® uncoated or Avastin® coated with titanium oxide.
FIG. 51 is a table showing percentage of aggregates quantified from results presented in FIG. 50.

To determine the functionality of the mAbs, the binding kinetics were determined by Surface Plasmon Resonance (SPR). Results for Avastin® are depicted in FIGS. 43-44. The data suggests that Avastin® coated with titanium oxide exhibited four-fold tighter binding (as reflected by reduced KD) to target human FcRn receptor compared to uncoated Avastin®. Results for Herceptin® are depicted in FIGS. 45-46. The data suggests that Herceptin® coated with aluminum oxide exhibited similar binding (as reflected by similar KD value) to target human FcRn receptor compared to uncoated Herceptin®.

To determine structural integrity and aggregation of the metal oxide coated mAbs over a period of 10 days at 80° C. the secondary structure of mAbs was measured by Fourier Transform Infrared Spectroscopy analysis (FTIR), the tertiary structure of mAbs was measured by intrinsic and extrinsic fluorescence analysis, and profile of size variants was measured by size exclusion chromatography (SEC). Results for Avastin® are depicted in FIGS. 47-51. The data suggests that Avastin® coated with titanium oxide exhibits little to no change at level of secondary structure or tertiary structure of mAb as detected by FTIR and fluorescence analysis, respectively, compared to uncoated Avastin®. The data also suggests that Avastin® coated with titanium oxide exhibits reduced accumulation rate of aggregates as determined by SEC compared to uncoated Avastin®. Results for Herceptin® are depicted in FIGS. 52-56. The data suggests that Herceptin® coated with titanium oxide exhibits little to no change at level of secondary structure or tertiary structure of mAb as detected by FTIR and fluorescence analysis, respectively, compared to uncoated Herceptin®. The data also suggests that Herceptin® coated with titanium oxide exhibits similar accumulation rate of aggregates as determined by SEC compared to uncoated Herceptin®.

CONCLUSION

This Example demonstrates that encapsulation of two different lyophilized mAbs by metal coatings does not confer significant decreases to mAb structure, stability, or ability to bind target polypeptides—e.g., human FcRn. Of note, Herceptin® coated by titanium oxide exhibited four-fold tighter binding (as reflected by reduced KD) to target human FcRn receptor compared to uncoated Avastin®. Also of note, Avastin® coated with titanium oxide exhibits reduced accumulation rate of aggregates at 80° C. over 10 days as determined by SEC compared to uncoated Avastin®. Applicants conclude a skilled practitioner could test different methods or parameters, as described herein, to generate lyophilized mAbs coated with select metal coatings that do not have significantly reduced mAb structure, stability, or ability to bind target polypeptides.

What is claimed is:

1. A method of preparing a pharmaceutical composition comprising a drug-containing core enclosed by one or more metal oxide materials, the method comprising the sequential steps of:
    (a) loading particles comprising the drug into a reactor, wherein the particles have a median particle size, on a volume average basis between 0.1 µm and 1000 µm;
    (b) applying a vaporous or gaseous metal precursor to the particles in the reactor;
    (c) performing one or more pump-purge cycles of the reactor using an inert gas;
    (d) applying vaporous or gaseous water as an oxidant to the particles in the reactor;
    (e) performing one or more pump-purge cycles of the reactor using the inert gas; and
    (f) repeating steps (b)-(e) one or more times to increase the total thickness of the one or more metal oxide materials that enclose the core, wherein the particles remain in the reactor during the repeated steps, each pump-purge cycle comprises flowing the inert gas into the reactor chamber to a desired pressure and after a delay time pumping the inert gas out of the reactor until the pressure of the inert gas is below 1 torr and repeating the steps of flowing the inert gas into the reactor chamber to a desired pressure and after a delay time pumping the inert gas out of the reactor until the pressure of the inert gas is below 1 torr, the temperature of the particles does not exceed 35° C., thereby producing a pharmaceutical composition comprising a drug containing core enclosed by one or more metal oxide materials,
    wherein the one or more metal oxide materials are selected from the group consisting of: aluminum oxide, titanium oxide, iron oxide, gallium oxide, magnesium oxide, zinc oxide, niobium oxide, hafnium oxide, tantalum oxide, lanthanum oxide, and zirconium dioxide.

2. The method of claim 1, wherein the reactor pressure is allowed to stabilize following step (a), step (b), and/or step (d).

3. The method of claim 1, wherein a subset of vapor or gaseous content is pumped out prior to step (c) and/or step (e).

4. The method of claim 1, wherein the particles comprise a drug and one or more pharmaceutically acceptable excipients.

5. The method of claim 1, wherein the particles have a median particle size, on a volume average basis between 0.1 µm and 1000 µm.

6. The method of claim 1, wherein the pharmaceutical composition is removed from the reactor and admixed with a pharmaceutically acceptable diluent or carrier.

7. The method of claim 1, wherein the particles consist essentially of the drug.

8. The method of claim 1, wherein the drug is a small molecule, virus particle, polypeptide, polynucleotide, a composition comprising polypeptide and lipid, or a composition comprising polynucleotide and lipid.

9. The method of claim 1, wherein the one or more metal oxide materials are selected from the group consisting of: aluminum oxide and titanium oxide.

10. The method of claim 1, wherein the reactor contents are agitated prior to and/or during step (b), step (c), and/or step (e).

11. The method of claim 1, wherein the temperature of the particles remains between 22° C. and 35° C.

12. The method of claim 1, wherein the inert gas is nitrogen gas or a noble gas.

13. The method of claim 12, wherein the inert gas is nitrogen gas.

14. The method of claim 1, wherein the drug is a small molecule drug that is selected from the group consisting of: acetaminophen, clarithromycin, azithromycin, ibuprofen, fluticasone propionate, salmeterol, pazopanib HC1, palbociclib, and amoxicillin potassium clavulanate.

15. The method of claim 1, wherein the drug is a small molecule drug that is selected from the group consisting of: clarithromycin, clarithromycin carbomer complex, pazopanib HC1, palbociclib, and amoxicillin potassium clavulanate.

16. The method of claim 1, wherein step (c) is repeated between 6 and 20 additional times.

17. The method of claim 1, wherein step (e) is repeated between 1 and 10 additional times.

18. The method of claim 1, wherein the one or more metal oxide materials are selected from the group consisting of aluminum oxide, titanium oxide, and zinc oxide.

* * * * *

UNITED STATES PATENT AND TRADEMARK OFFICE
CERTIFICATE OF CORRECTION

| | |
|---|---|
| PATENT NO. | : 12,005,145 B2 |
| APPLICATION NO. | : 17/695687 |
| DATED | : June 11, 2024 |
| INVENTOR(S) | : Colin C. Neikirk and Jonathan Frankel |

It is certified that error appears in the above-identified patent and that said Letters Patent is hereby corrected as shown below:

In the Claims

In Column 21, Line 11, Claim 1, delete "drug- containing" and insert -- drug-containing --.

In Column 22, Line 34, Claim 14, delete "HC1," and insert -- HCl, --.

In Column 22, Line 39, Claim 15, delete "HC1," and insert -- HCl, --.

Signed and Sealed this
Thirteenth Day of August, 2024

*Katherine Kelly Vidal*

Katherine Kelly Vidal
*Director of the United States Patent and Trademark Office*